(12) United States Patent
Wolf et al.

(10) Patent No.: US 11,766,296 B2
(45) Date of Patent: Sep. 26, 2023

(54) TRACKING SYSTEM FOR IMAGE-GUIDED SURGERY

(71) Applicant: AUGMEDICS LTD., Yokneam (IL)

(72) Inventors: Stuart Wolf, Yokneam (IL); Nissan Elimelech, Beerotaim (IL)

(73) Assignee: AUGMEDICS LTD., Yokneam Illit (IL)

( * ) Notice: Subject to any disclaimer, the term of this patent is extended or adjusted under 35 U.S.C. 154(b) by 0 days.

(21) Appl. No.: 16/200,144

(22) Filed: Nov. 26, 2018

(65) Prior Publication Data

US 2020/0163723 A1 May 28, 2020

(51) Int. Cl.
| | |
|---|---|
| *A61B 34/20* | (2016.01) |
| *A61B 90/00* | (2016.01) |
| *A61B 34/00* | (2016.01) |
| *A61B 34/10* | (2016.01) |
| *G02B 27/00* | (2006.01) |
| *G02B 27/01* | (2006.01) |

(52) U.S. Cl.
CPC .............. *A61B 34/20* (2016.02); *A61B 34/25* (2016.02); *A61B 90/36* (2016.02); *G02B 27/0093* (2013.01); *G02B 27/0172* (2013.01); *A61B 34/10* (2016.02); *A61B 2034/2055* (2016.02); *A61B 2090/365* (2016.02); *G02B 2027/0178* (2013.01)

(58) Field of Classification Search
None
See application file for complete search history.

(56) References Cited

U.S. PATENT DOCUMENTS

| | | |
|---|---|---|
| 4,459,358 A | 7/1984 | Berke |
| 4,863,238 A | 9/1989 | Brewster |
| (Continued) | | |

FOREIGN PATENT DOCUMENTS

| | | |
|---|---|---|
| CA | 3022448 A1 | 2/2018 |
| CN | 101379412 A | 3/2009 |
| (Continued) | | |

OTHER PUBLICATIONS

US 11,395,705 B2, 09/2022, Lang (withdrawn)
(Continued)

*Primary Examiner* — Katherine L Fernandez
*Assistant Examiner* — Farouk A Bruce
(74) *Attorney, Agent, or Firm* — KNOBBE, MARTENS, OLSON & BEAR, LLP

(57) ABSTRACT

Apparatus and methods are described including tracking a tool portion and a patient marker from a first line of sight, using a first tracking device disposed upon a first head-mounted device that includes a display. The tool portion and the patient marker are tracked from a second line of sight, using a second tracking device. When a portion of the patient marker and the tool portion are both within the first line of sight, an augmented reality image is generated upon the first display based upon data received from the first tracking device and without using data from the second tracking device. When at least the patient marker portion and the tool portion are not both within the first line of sight, a virtual image of the tool and anatomy of the patient is generated using data received from the second tracking device. Other applications are also described.

26 Claims, 6 Drawing Sheets

(56) References Cited

U.S. PATENT DOCUMENTS

| | | |
|---|---|---|
| 5,441,042 A | 8/1995 | Putman |
| 5,442,146 A | 8/1995 | Bell |
| 5,510,832 A | 4/1996 | Garcia |
| 5,771,121 A | 6/1998 | Hentschke |
| 5,792,046 A | 8/1998 | Dobrovolny |
| 5,841,507 A | 11/1998 | Barnes et al. |
| 6,006,126 A | 12/1999 | Cosman |
| 6,125,164 A | 9/2000 | Murphy |
| 6,227,667 B1 | 5/2001 | Halldorsson |
| 6,256,529 B1 | 7/2001 | Holupka et al. |
| 6,314,310 B1 | 11/2001 | Ben-Haim et al. |
| 6,444,192 B1 | 9/2002 | Mattrey |
| 6,449,090 B1 | 9/2002 | Omar |
| 6,549,645 B1 | 4/2003 | Oikawa |
| 6,609,022 B2 | 8/2003 | Vilsmeier et al. |
| 6,610,009 B2 | 8/2003 | Person |
| 6,675,040 B1 | 1/2004 | Cosman |
| 6,737,425 B1 | 5/2004 | Yamamoto |
| 6,740,882 B2 | 5/2004 | Weinberg |
| 6,757,068 B2 | 6/2004 | Foxlin |
| 6,759,200 B1 | 7/2004 | Stanton |
| 6,856,324 B2 | 2/2005 | Sauer |
| 6,856,826 B2 | 2/2005 | Seeley et al. |
| 6,891,518 B2 | 5/2005 | Sauer et al. |
| 6,919,867 B2 | 7/2005 | Sauer |
| 6,921,167 B2 | 7/2005 | Nagata |
| 6,966,668 B2 | 11/2005 | Cugini |
| 6,980,849 B2 | 12/2005 | Sasso |
| 6,993,374 B2 | 1/2006 | Sasso |
| 6,997,552 B1 | 2/2006 | Hung |
| 7,043,961 B2 | 5/2006 | Pandey et al. |
| 7,103,233 B2 | 9/2006 | Stearns |
| 7,107,091 B2 | 9/2006 | Jutras et al. |
| 7,112,656 B2 | 9/2006 | Desnoyers |
| 7,141,812 B2 | 11/2006 | Appleby |
| 7,157,459 B2 | 1/2007 | Ohta |
| 7,169,785 B2 | 1/2007 | Timmer |
| 7,171,255 B2 | 1/2007 | Holupka et al. |
| 7,187,792 B2 | 3/2007 | Fu |
| 7,194,295 B2 | 3/2007 | Vilsmeier |
| 7,229,078 B2 | 6/2007 | Lechot |
| 7,231,076 B2 | 6/2007 | Fu |
| 7,259,266 B2 | 8/2007 | Carter |
| 7,260,426 B2 | 8/2007 | Schweikard |
| 7,281,826 B2 | 10/2007 | Huang |
| 7,320,556 B2 | 1/2008 | Vagn-Erik |
| 7,330,578 B2 | 2/2008 | Wang |
| 7,359,535 B2 | 4/2008 | Salla |
| 7,364,314 B2 | 4/2008 | Nilsen et al. |
| 7,379,077 B2 | 5/2008 | Bani-Hashemi |
| 7,431,453 B2 | 10/2008 | Hogan |
| 7,435,219 B2 | 10/2008 | Kim |
| 7,458,977 B2 | 12/2008 | McGinley |
| 7,462,852 B2 | 12/2008 | Appleby |
| 7,493,153 B2 | 2/2009 | Ahmed et al. |
| 7,505,617 B2 | 3/2009 | Fu |
| 7,507,968 B2 | 3/2009 | Wollenweber |
| 7,518,136 B2 | 4/2009 | Appleby |
| D592,691 S | 5/2009 | Chang |
| D592,692 S | 5/2009 | Chang |
| D592,693 S | 5/2009 | Chang |
| 7,542,791 B2 | 6/2009 | Mire |
| 7,556,428 B2 | 7/2009 | Sukovic et al. |
| 7,567,834 B2 | 7/2009 | Clayton |
| D602,620 S | 10/2009 | Cristoforo |
| 7,605,826 B2 | 10/2009 | Sauer |
| 7,607,775 B2 | 10/2009 | Hermanson |
| 7,620,223 B2 | 11/2009 | Xu |
| 7,630,753 B2 | 12/2009 | Simon et al. |
| 7,633,501 B2 | 12/2009 | Wood |
| 7,645,050 B2 | 1/2010 | Wilt |
| 7,689,019 B2 | 3/2010 | Boese |
| 7,689,042 B2 | 3/2010 | Brunner |
| 7,689,320 B2 | 3/2010 | Prisco |
| 7,699,486 B1 | 4/2010 | Beiner |
| 7,699,793 B2 | 4/2010 | Gotte |
| 7,719,769 B2 | 5/2010 | Sugihara et al. |
| D617,825 S | 6/2010 | Chang |
| D619,285 S | 7/2010 | Cristoforo |
| 7,758,204 B2 | 7/2010 | Klipstein |
| 7,768,702 B2 | 8/2010 | Hirose et al. |
| 7,769,236 B2 | 8/2010 | Fiala |
| 7,774,044 B2 | 8/2010 | Sauer et al. |
| D628,307 S | 11/2010 | Krause-Bonte |
| 7,831,096 B2 | 11/2010 | Williamson |
| 7,835,778 B2 | 11/2010 | Foley |
| 7,835,784 B2 | 11/2010 | Mire et al. |
| 7,837,987 B2 | 11/2010 | Shi |
| 7,840,256 B2 | 11/2010 | Lakin et al. |
| 7,853,305 B2 | 12/2010 | Simon |
| 7,854,705 B2 | 12/2010 | Pawluczyk |
| 7,857,271 B2 | 12/2010 | Lees |
| 7,860,282 B2 | 12/2010 | Boese |
| D630,766 S | 1/2011 | Harbin |
| 7,865,269 B2 | 1/2011 | Prisco |
| 7,874,686 B2 | 1/2011 | Rossner et al. |
| 7,881,770 B2 | 2/2011 | Melkent et al. |
| 7,893,413 B1 | 2/2011 | Appleby |
| 7,894,649 B2 | 2/2011 | Fu |
| 7,938,553 B1 | 5/2011 | Beiner |
| 7,945,310 B2 | 5/2011 | Gattani |
| 7,953,471 B2 | 5/2011 | Clayton |
| 7,974,677 B2 | 7/2011 | Mire |
| 7,985,756 B2 | 7/2011 | Barlow |
| 7,991,557 B2 | 8/2011 | Liew |
| 7,993,353 B2 | 8/2011 | Robner et al. |
| 8,022,984 B2 | 9/2011 | Cheong |
| 8,045,266 B2 | 10/2011 | Nakamura |
| 8,060,181 B2 | 11/2011 | Ponce |
| 8,068,896 B2 | 11/2011 | Daghighian |
| 8,077,943 B2 | 12/2011 | Wiliams |
| 8,085,075 B2 | 12/2011 | Huffman |
| 8,085,897 B2 | 12/2011 | Morton |
| 8,090,175 B2 | 1/2012 | Fu |
| 8,092,400 B2 | 1/2012 | Warkentine |
| 8,108,072 B2 | 1/2012 | Zhao |
| 8,112,292 B2 | 2/2012 | Simon |
| 8,120,847 B2 | 2/2012 | Chang |
| 8,155,479 B2 | 4/2012 | Hoffman |
| 8,180,429 B2 | 5/2012 | Sasso |
| 8,208,599 B2 | 6/2012 | Ye |
| 8,221,402 B2 | 7/2012 | Francischelli |
| 8,253,778 B2 | 8/2012 | Takahashi |
| 8,271,069 B2 | 9/2012 | Jascob et al. |
| 8,285,021 B2 | 10/2012 | Boese |
| 8,305,685 B2 | 11/2012 | Heine |
| 8,306,305 B2 | 11/2012 | Porat et al. |
| 8,309,932 B2 | 11/2012 | Haselman |
| 8,317,320 B2 | 11/2012 | Huang |
| 8,335,553 B2 | 12/2012 | Rubner |
| 8,369,925 B2 | 2/2013 | Giesel |
| 8,386,022 B2 | 2/2013 | Jutras et al. |
| 8,394,144 B2 | 3/2013 | Zehavi |
| 8,444,266 B2 | 5/2013 | Waters |
| 8,467,851 B2 | 6/2013 | Mire et al. |
| 8,469,902 B2 | 6/2013 | Dick |
| 8,531,394 B2 | 9/2013 | Maltz |
| 8,540,364 B2 | 9/2013 | Waters |
| 8,545,012 B2 | 10/2013 | Waters |
| 8,556,883 B2 | 10/2013 | Saleh |
| 8,559,596 B2 | 10/2013 | Thomson |
| 8,567,945 B2 | 10/2013 | Waters |
| 8,600,477 B2 | 12/2013 | Beyar |
| 8,634,897 B2 | 1/2014 | Simon |
| 8,674,902 B2 | 3/2014 | Park |
| 8,690,776 B2 | 4/2014 | Razzaque et al. |
| 8,692,845 B2 | 4/2014 | Fedorovskaya et al. |
| 8,693,632 B2 | 4/2014 | Allison |
| 8,694,075 B2 | 4/2014 | Groszmann |
| 8,699,765 B2 | 4/2014 | Hao |
| 8,705,829 B2 | 4/2014 | Frank |
| 8,746,887 B2 | 6/2014 | Shestak |
| 8,786,689 B1 | 7/2014 | Liu |
| 8,831,706 B2 | 9/2014 | Fu |

(56) References Cited

U.S. PATENT DOCUMENTS

| | | |
|---|---|---|
| 8,836,768 B1 | 9/2014 | Rafii et al. |
| 8,848,977 B2 | 9/2014 | Bammer et al. |
| 8,855,395 B2 | 10/2014 | Baturin |
| 8,878,900 B2 | 11/2014 | Yang et al. |
| 8,890,772 B2 | 11/2014 | Woo |
| 8,890,773 B1 | 11/2014 | Pederson |
| 8,890,943 B2 | 11/2014 | Lee |
| 8,897,514 B2 | 11/2014 | Feikas |
| 8,903,150 B2 | 12/2014 | Star-Lack |
| 8,917,268 B2 | 12/2014 | Johnsen |
| 8,920,776 B2 | 12/2014 | Gaiger |
| 8,942,455 B2 | 1/2015 | Chou |
| 8,950,877 B2 | 2/2015 | Northey et al. |
| 8,969,829 B2 | 3/2015 | Wollenweber |
| 8,989,349 B2 | 3/2015 | Thomson |
| 8,992,580 B2 | 3/2015 | Bar |
| 8,994,795 B2 | 3/2015 | Oh |
| 9,004,711 B2 | 4/2015 | Gerolemou |
| 9,057,759 B2 | 6/2015 | Klingenbeck |
| 9,066,751 B2 | 6/2015 | Sasso |
| 9,081,436 B1 | 7/2015 | Berme |
| 9,085,643 B2 | 7/2015 | Svanborg |
| 9,100,643 B2 | 8/2015 | McDowall |
| 9,111,175 B2 | 8/2015 | Strommer |
| 9,125,556 B2 | 9/2015 | Zehavi |
| 9,129,372 B2 | 9/2015 | Kriston |
| 9,149,317 B2 | 10/2015 | Arthur et al. |
| 9,179,984 B2 | 11/2015 | Teichman et al. |
| D746,354 S | 12/2015 | Chang |
| 9,208,916 B2 | 12/2015 | Appleby |
| 9,220,573 B2 | 12/2015 | Kendrick et al. |
| 9,235,934 B2 | 1/2016 | Mandella |
| 9,247,240 B2 | 1/2016 | Park |
| 9,265,572 B2 | 2/2016 | Fuchs et al. |
| 9,269,192 B2 | 2/2016 | Kobayashi |
| 9,283,052 B2 | 3/2016 | Ponce |
| 9,320,474 B2 | 4/2016 | Demri |
| 9,323,055 B2 | 4/2016 | Baillot |
| 9,330,477 B2 | 5/2016 | Rappel |
| 9,335,567 B2 | 5/2016 | Nakamura |
| 9,341,704 B2 | 5/2016 | Picard |
| 9,344,686 B2 | 5/2016 | Moharir |
| 9,349,066 B2 | 5/2016 | Koo |
| 9,349,520 B2 | 5/2016 | Demetriou |
| 9,378,558 B2 | 6/2016 | Kajiwara et al. |
| 9,380,287 B2 | 6/2016 | Nistico |
| 9,387,008 B2 | 7/2016 | Sarvestani |
| 9,395,542 B2 | 7/2016 | Tilleman et al. |
| 9,414,041 B2 | 8/2016 | Ko |
| 9,424,611 B2 | 8/2016 | Kanjirathinkal et al. |
| 9,424,641 B2 | 8/2016 | Wiemker |
| 9,438,894 B2 | 9/2016 | Park |
| 9,443,488 B2 | 9/2016 | Borenstein |
| 9,456,878 B2 | 10/2016 | Macfarlane et al. |
| 9,465,235 B2 | 10/2016 | Chang |
| 9,468,373 B2 | 10/2016 | Larsen |
| 9,470,908 B1 | 10/2016 | Frankel |
| 9,473,766 B2 | 10/2016 | Douglas |
| 9,495,585 B2 | 11/2016 | Bicer et al. |
| 9,498,231 B2 | 11/2016 | Haider et al. |
| 9,513,495 B2 | 12/2016 | Waters |
| 9,521,966 B2 | 12/2016 | Schwartz |
| 9,526,443 B1 | 12/2016 | Berme |
| 9,532,846 B2 | 1/2017 | Nakamura |
| 9,532,849 B2 | 1/2017 | Anderson et al. |
| 9,538,962 B1 | 1/2017 | Hannaford et al. |
| 9,545,233 B2 | 1/2017 | Sirpad |
| 9,546,779 B2 | 1/2017 | Rementer |
| 9,561,095 B1 | 2/2017 | Nguyen |
| 9,565,415 B2 | 2/2017 | Zhang et al. |
| 9,572,661 B2 | 2/2017 | Robin |
| 9,629,595 B2 | 4/2017 | Walker |
| 9,633,431 B2 | 4/2017 | Merlet |
| 9,672,597 B2 | 6/2017 | Amiot |
| 9,672,640 B2 | 6/2017 | Kleiner |
| 9,675,306 B2 | 6/2017 | Morton |
| 9,675,319 B1 | 6/2017 | Razzaque |
| RE46,463 E | 7/2017 | Feinbloom |
| 9,710,968 B2 | 7/2017 | Dillavou et al. |
| 9,713,502 B2 | 7/2017 | Finkman |
| 9,724,119 B2 | 8/2017 | Hissong |
| 9,724,165 B2 | 8/2017 | Arata et al. |
| 9,726,888 B2 | 8/2017 | Giartisio |
| 9,728,006 B2 | 8/2017 | Varga |
| 9,729,831 B2 | 8/2017 | Birnkrant |
| 9,757,034 B2 | 9/2017 | Desjardins |
| 9,757,087 B2 | 9/2017 | Simon |
| 9,766,441 B2 | 9/2017 | Rappel |
| 9,767,608 B2 | 9/2017 | Lee et al. |
| 9,770,203 B1 | 9/2017 | Berme |
| 9,772,102 B1 | 9/2017 | Ferguson |
| 9,772,495 B2 | 9/2017 | Tam |
| 9,791,138 B1 | 10/2017 | Feinbloom |
| 9,800,995 B2 | 10/2017 | Libin |
| 9,805,504 B2 | 10/2017 | Zhang |
| 9,808,148 B2 | 11/2017 | Miller |
| 9,844,413 B2 | 12/2017 | Daon et al. |
| 9,851,080 B2 | 12/2017 | Wilt |
| 9,861,446 B2 | 1/2018 | Lang |
| 9,864,214 B2 | 1/2018 | Fass |
| 9,872,733 B2 | 1/2018 | Shoham et al. |
| 9,877,642 B2 | 1/2018 | Duret |
| 9,885,465 B2 | 2/2018 | Nguyen |
| 9,886,552 B2 | 2/2018 | Dillavou et al. |
| 9,892,564 B1 | 2/2018 | Cvetko et al. |
| 9,898,866 B2 | 2/2018 | Fuchs et al. |
| 9,901,414 B2 | 2/2018 | Lively |
| 9,911,187 B2 | 3/2018 | Steinle |
| 9,927,611 B2 | 3/2018 | Rudy |
| 9,928,629 B2 | 3/2018 | Benishti et al. |
| 9,940,750 B2 | 4/2018 | Dillavou et al. |
| 9,943,374 B2 | 4/2018 | Merritt et al. |
| 9,947,110 B2 | 4/2018 | Haimerl |
| 9,956,054 B2 | 5/2018 | Aguirre-Valencia |
| 9,959,629 B2 | 5/2018 | Dillavou et al. |
| 9,968,297 B2 | 5/2018 | Connor |
| 9,980,780 B2 | 5/2018 | Lang |
| 9,986,228 B2 | 5/2018 | Woods |
| 10,010,379 B1 | 7/2018 | Gibby et al. |
| 10,013,531 B2 | 7/2018 | Richards |
| 10,016,243 B2 | 7/2018 | Esterberg |
| 10,022,065 B2 | 7/2018 | Yishai et al. |
| 10,022,104 B2 | 7/2018 | Sell et al. |
| 10,023,615 B2 | 7/2018 | Bonny |
| 10,026,015 B2 | 7/2018 | Cavusoglu |
| 10,034,713 B2 | 7/2018 | Yang et al. |
| 10,046,165 B2 | 8/2018 | Frewin |
| 10,066,816 B2 | 9/2018 | Chang |
| 10,073,515 B2 | 9/2018 | Awdeh |
| 10,080,616 B2 | 9/2018 | Wilkinson et al. |
| 10,082,680 B2 | 9/2018 | Chang |
| 10,085,709 B2 | 10/2018 | Lavallee et al. |
| 10,107,483 B2 | 10/2018 | Oren |
| 10,108,833 B2 | 10/2018 | Hong et al. |
| 10,123,840 B2 | 11/2018 | Dorman |
| 10,132,483 B1 | 11/2018 | Feinbloom |
| 10,134,166 B2 | 11/2018 | Benishti et al. |
| 10,134,194 B2 | 11/2018 | Kepner |
| 10,139,652 B2 | 11/2018 | Windham |
| 10,139,920 B2 | 11/2018 | Isaacs |
| 10,142,496 B1 | 11/2018 | Rao |
| 10,151,928 B2 | 12/2018 | Ushakov |
| 10,154,239 B2 | 12/2018 | Casas |
| 10,159,530 B2 | 12/2018 | Lang |
| 10,166,079 B2 | 1/2019 | McLachlin et al. |
| 10,175,507 B2 | 1/2019 | Nakamura |
| 10,175,753 B2 | 1/2019 | Boesen |
| 10,181,361 B2 | 1/2019 | Dillavou et al. |
| 10,186,055 B2 | 1/2019 | Takahashi |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |

(56) References Cited

U.S. PATENT DOCUMENTS

| | | |
|---|---|---|
| 10,197,816 B2 | 2/2019 | Waisman |
| 10,207,315 B2 | 2/2019 | Appleby |
| 10,230,719 B2 | 3/2019 | Vaugn |
| 10,231,893 B2 | 3/2019 | Lei |
| 10,235,606 B2 | 3/2019 | Miao |
| 10,240,769 B1 | 3/2019 | Braganca |
| 10,247,965 B2 | 4/2019 | Ton |
| 10,251,724 B2 | 4/2019 | McLachlin et al. |
| 10,278,777 B1 | 5/2019 | Lang |
| 10,292,768 B2 | 5/2019 | Lang |
| 10,296,805 B2 | 5/2019 | Yang et al. |
| 10,326,975 B2 | 6/2019 | Casas |
| 10,352,543 B1 | 7/2019 | Braganca |
| 10,357,146 B2 | 7/2019 | Fiebel |
| 10,357,574 B2 | 7/2019 | Hilderbrand |
| 10,366,489 B2 | 7/2019 | Boettger et al. |
| 10,368,947 B2 | 8/2019 | Lang |
| 10,368,948 B2 | 8/2019 | Tripathi |
| 10,386,645 B2 | 8/2019 | Shousha |
| 10,405,927 B1 | 9/2019 | Lang |
| 10,419,655 B2 | 9/2019 | Sivan |
| 10,420,626 B2 | 9/2019 | Tokuda et al. |
| 10,420,813 B2 | 9/2019 | Newell-Rogers |
| 10,424,115 B2 | 9/2019 | Ellerbrock |
| 10,431,008 B2 | 10/2019 | Djajadiningrat |
| 10,433,814 B2 | 10/2019 | Razzaque |
| 10,434,335 B2 | 10/2019 | Takahashi |
| 10,448,003 B2 | 10/2019 | Grafenberg |
| 10,449,040 B2 | 10/2019 | Lashinski |
| 10,453,187 B2 | 10/2019 | Peterson |
| 10,463,434 B2 | 11/2019 | Siegler et al. |
| 10,465,892 B1 | 11/2019 | Feinbloom |
| 10,470,732 B2 | 11/2019 | Baumgart |
| 10,473,314 B1 | 11/2019 | Braganca |
| 10,485,989 B2 | 11/2019 | Jordan |
| 10,488,663 B2 | 11/2019 | Choi |
| 10,499,997 B2 | 12/2019 | Weinstein et al. |
| 10,504,231 B2 | 12/2019 | Fiala |
| 10,507,066 B2 | 12/2019 | DiMaio |
| 10,511,822 B2 | 12/2019 | Casas |
| 10,517,544 B2 | 12/2019 | Taguchi |
| 10,537,395 B2 | 1/2020 | Perez |
| 10,540,780 B1 | 1/2020 | Cousins |
| 10,543,485 B2 | 1/2020 | Ismagilov |
| 10,546,423 B2 | 1/2020 | Jones et al. |
| 10,548,557 B2 | 2/2020 | Lim |
| 10,555,775 B2 | 2/2020 | Hoffman |
| 10,571,716 B2 | 2/2020 | Chapiro |
| 10,573,087 B2 | 2/2020 | Gallop |
| 10,602,114 B2 | 2/2020 | Casas |
| 10,577,630 B2 | 3/2020 | Zhang |
| 10,586,400 B2 | 3/2020 | Douglas |
| 10,592,748 B1 | 3/2020 | Cousins |
| 10,595,716 B2 | 3/2020 | Nazareth |
| 10,601,950 B2 | 3/2020 | Devam et al. |
| 10,603,113 B2 | 3/2020 | Lang |
| 10,603,133 B2 | 3/2020 | Wang et al. |
| 10,606,085 B2 | 3/2020 | Toyama |
| 10,594,998 B1 | 4/2020 | Casas |
| 10,610,172 B2 | 4/2020 | Hummel et al. |
| 10,610,179 B2 | 4/2020 | Altmann |
| 10,613,352 B2 | 4/2020 | Knoll |
| 10,617,566 B2 | 4/2020 | Esmonde |
| 10,620,460 B2 | 4/2020 | Carabin |
| 10,625,099 B2 | 4/2020 | Takahashi |
| 10,626,473 B2 | 4/2020 | Mariani |
| 10,631,907 B2 | 4/2020 | Zucker |
| 10,634,331 B1 | 4/2020 | Feinbloom |
| 10,638,080 B2 | 4/2020 | Ovchinnikov |
| 10,646,285 B2 | 5/2020 | Siemionow et al. |
| 10,650,594 B2 | 5/2020 | Jones |
| 10,652,525 B2 | 5/2020 | Woods |
| 10,660,715 B2 | 5/2020 | Dozeman |
| 10,663,738 B2 | 5/2020 | Carlvik |
| 10,682,112 B2 | 6/2020 | Pizaine |
| 10,682,767 B2 | 6/2020 | Grafenberg et al. |
| 10,687,901 B2 | 6/2020 | Thomas |
| 10,691,397 B1 | 6/2020 | Clements |
| 10,702,713 B2 | 7/2020 | Mori |
| 10,709,398 B2 | 7/2020 | Schweizer |
| 10,713,801 B2 | 7/2020 | Jordan |
| 10,716,643 B2 | 7/2020 | Justin et al. |
| 10,722,733 B2 | 7/2020 | Takahashi |
| 10,725,535 B2 | 7/2020 | Yu |
| 10,731,832 B2 | 8/2020 | Koo |
| 10,732,721 B1 | 8/2020 | Clements |
| 10,742,949 B2 | 8/2020 | Casas |
| 10,743,939 B1 | 8/2020 | Lang |
| 10,747,315 B2 | 8/2020 | Tungare |
| 10,777,094 B1 | 9/2020 | Rao |
| 10,777,315 B2 | 9/2020 | Zehavi |
| 10,781,482 B2 | 9/2020 | Gubatayao |
| 10,792,110 B2 | 10/2020 | Leung et al. |
| 10,799,296 B2 | 10/2020 | Lang |
| 10,799,316 B2 | 10/2020 | Sela et al. |
| 10,810,799 B2 | 10/2020 | Tepper et al. |
| 10,818,019 B2 | 10/2020 | Piat |
| 10,818,101 B2 | 10/2020 | Gallop et al. |
| 10,818,199 B2 | 10/2020 | Buras et al. |
| 10,825,563 B2 | 11/2020 | Gibby et al. |
| 10,831,943 B2 | 11/2020 | Santarone |
| 10,835,296 B2 | 11/2020 | Elimelech et al. |
| 10,838,206 B2 | 11/2020 | Fortin-Deschenes et al. |
| 10,839,629 B2 | 11/2020 | Jones |
| 10,839,956 B2 | 11/2020 | Beydoun et al. |
| 10,841,556 B2 | 11/2020 | Casas |
| 10,842,002 B2 | 11/2020 | Chang |
| 10,842,461 B2 | 11/2020 | Johnson et al. |
| 10,849,691 B2 | 12/2020 | Zucker |
| 10,849,693 B2 | 12/2020 | Lang |
| 10,849,710 B2 | 12/2020 | Liu |
| 10,861,236 B2 | 12/2020 | Geri et al. |
| 10,865,220 B2 | 12/2020 | Ebetino |
| 10,869,517 B1 | 12/2020 | Halpern |
| 10,872,472 B2 | 12/2020 | Watola |
| 10,877,262 B1 | 12/2020 | Luxembourg |
| 10,877,296 B2 | 12/2020 | Lindsey |
| 10,878,639 B2 | 12/2020 | Douglas |
| 10,893,260 B2 | 1/2021 | Trail et al. |
| 10,895,742 B2 | 1/2021 | Schneider |
| 10,895,743 B2 | 1/2021 | Dausmann |
| 10,898,151 B2 | 1/2021 | Harding et al. |
| 10,921,595 B2 | 2/2021 | Rakshit |
| 10,928,321 B2 | 2/2021 | Rawle |
| 10,928,638 B2 | 2/2021 | Ninan |
| 10,935,815 B1 | 3/2021 | Castaneda |
| 10,935,816 B2 | 3/2021 | Ban |
| 10,936,537 B2 | 3/2021 | Huston |
| 10,939,973 B2 | 3/2021 | DiMaio |
| 10,939,977 B2 | 3/2021 | Messinger et al. |
| 10,941,933 B2 | 3/2021 | Ferguson |
| 10,946,108 B2 | 3/2021 | Zhang |
| 10,950,338 B2 | 3/2021 | Douglas |
| 10,951,872 B2 | 3/2021 | Casas |
| 10,964,095 B1 | 3/2021 | Douglas |
| 10,964,124 B1 | 3/2021 | Douglas |
| 11,000,335 B2 | 5/2021 | Dorman |
| 11,006,093 B1 | 5/2021 | Hegyi |
| 11,013,560 B2 | 5/2021 | Lang |
| 11,013,562 B2 | 5/2021 | Marti |
| 11,013,573 B2 | 5/2021 | Chang |
| 11,013,900 B2 | 5/2021 | Malek |
| 11,019,988 B2 | 6/2021 | Fiebel |
| 11,027,027 B2 | 6/2021 | Manning |
| 11,029,147 B2 | 6/2021 | Abovitz et al. |
| 11,030,809 B2 | 6/2021 | Wang |
| 11,041,173 B2 | 6/2021 | Zhang |
| 11,045,663 B2 | 6/2021 | Mori |
| 11,049,293 B2 | 6/2021 | Chae |
| 11,050,990 B2 | 6/2021 | Casas |
| 11,057,505 B2 | 7/2021 | Dharmatilleke |
| 11,058,390 B1 | 7/2021 | Douglas |
| 11,061,257 B1 | 7/2021 | Hakim |
| 11,065,062 B2 | 7/2021 | Frushour |

(56) References Cited

U.S. PATENT DOCUMENTS

| | | |
|---|---|---|
| 11,067,387 B2 | 7/2021 | Marell |
| 11,071,497 B2 | 7/2021 | Hallack |
| 11,087,039 B2 | 8/2021 | Duff |
| 11,090,019 B2 | 8/2021 | Siemionow et al. |
| 11,097,129 B2 | 8/2021 | Sakata |
| 11,099,376 B1 | 8/2021 | Steier |
| 11,103,320 B2 | 8/2021 | LeBoeuf |
| 11,109,762 B1 | 9/2021 | Steier |
| 11,122,164 B2 | 9/2021 | Gigante |
| 11,123,604 B2 | 9/2021 | Fung |
| 11,135,015 B2 | 10/2021 | Crawford |
| 11,135,016 B2 | 10/2021 | Frielinghaus et al. |
| 11,141,221 B2 | 10/2021 | Hobeika |
| 11,153,549 B2 | 10/2021 | Casas |
| 11,153,555 B1 | 11/2021 | Healy et al. |
| 11,163,176 B2 | 11/2021 | Karafin |
| 11,164,324 B2 | 11/2021 | Liu |
| 11,166,006 B2 | 11/2021 | Hegyi |
| 11,172,990 B2 | 11/2021 | Lang |
| 11,179,136 B2 | 11/2021 | Kohli |
| 11,180,557 B2 | 11/2021 | Noelle |
| 11,185,891 B2 | 11/2021 | Cousins |
| 11,202,682 B2 | 12/2021 | Staunton |
| 11,207,150 B2 | 12/2021 | Healy |
| 11,217,028 B2 | 1/2022 | Jones |
| 11,224,763 B2 | 1/2022 | Takahashi |
| 11,227,417 B2 | 1/2022 | Berlinger |
| 11,253,323 B2 | 2/2022 | Hughes et al. |
| 11,257,190 B2 | 2/2022 | Mao |
| 11,263,772 B2 | 3/2022 | Siemionow et al. |
| 11,272,151 B2 | 3/2022 | Casas |
| 11,278,359 B2 | 3/2022 | Siemionow et al. |
| 11,278,413 B1 | 3/2022 | Lang |
| 11,280,480 B2 | 3/2022 | Wilt |
| 11,284,846 B2 | 3/2022 | Graumann |
| 11,311,341 B2 | 3/2022 | Lang |
| 11,291,521 B2 | 4/2022 | Im |
| 11,294,167 B2 | 4/2022 | Ishimoda |
| 11,297,285 B2 | 4/2022 | Pierce |
| 11,300,252 B2 | 4/2022 | Nguyen |
| 11,307,402 B2 | 4/2022 | Steier |
| 11,317,973 B2 | 5/2022 | Calloway |
| 11,348,257 B2 | 5/2022 | Lang |
| 11,350,072 B1 | 5/2022 | Casas |
| 11,351,006 B2 | 6/2022 | Aferzon |
| 11,360,315 B2 | 6/2022 | Tu |
| 11,382,699 B2 | 7/2022 | Wassall |
| 11,382,700 B2 | 7/2022 | Calloway |
| 11,382,712 B2 | 7/2022 | Elimelech et al. |
| 11,382,713 B2 | 7/2022 | Healy |
| 11,389,252 B2 | 7/2022 | Gera et al. |
| 11,432,828 B1 | 9/2022 | Lang |
| 11,432,931 B2 | 9/2022 | Lang |
| 11,452,568 B2 | 9/2022 | Lang |
| 11,460,915 B2 | 10/2022 | Frielinghaus |
| 11,461,983 B2 | 10/2022 | Jones |
| 11,464,581 B2 | 10/2022 | Calloway |
| 11,483,532 B2 | 10/2022 | Casas |
| 2002/0082498 A1 | 6/2002 | Wendt et al. |
| 2003/0117393 A1 | 6/2003 | Sauer et al. |
| 2003/0130576 A1 | 7/2003 | Seeley |
| 2003/0156144 A1 | 8/2003 | Morita |
| 2003/0210812 A1 | 11/2003 | Khamene et al. |
| 2003/0225329 A1 | 12/2003 | Rossner et al. |
| 2004/0030237 A1 | 2/2004 | Lee et al. |
| 2004/0138556 A1 | 7/2004 | Cosman |
| 2005/0017972 A1 | 1/2005 | Poole |
| 2005/0024586 A1 | 2/2005 | Teiwes et al. |
| 2005/0119639 A1 | 6/2005 | McCombs et al. |
| 2005/0203367 A1* | 9/2005 | Ahmed ............... A61B 90/36 600/407 |
| 2005/0215879 A1 | 9/2005 | Chuanggui |
| 2006/0134198 A1 | 6/2006 | Tawa |
| 2006/0176242 A1 | 8/2006 | Jaramaz et al. |
| 2007/0018975 A1 | 1/2007 | Chuanggui et al. |
| 2008/0007645 A1 | 1/2008 | Mccutchen |
| 2008/0085033 A1 | 4/2008 | Haven et al. |
| 2008/0159612 A1 | 7/2008 | Fu |
| 2008/0183065 A1 | 7/2008 | Goldbach |
| 2008/0221625 A1 | 9/2008 | Hufner et al. |
| 2008/0262812 A1 | 10/2008 | Arata et al. |
| 2009/0018437 A1 | 1/2009 | Cooke |
| 2009/0036902 A1 | 5/2009 | Dimaio et al. |
| 2009/0227847 A1 | 9/2009 | Tepper et al. |
| 2009/0300540 A1 | 12/2009 | Russell |
| 2010/0114110 A1 | 5/2010 | Taft et al. |
| 2010/0149073 A1 | 6/2010 | Chaum et al. |
| 2010/0210939 A1 | 8/2010 | Hartmann et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0216060 A1 | 9/2011 | Weising et al. |
| 2011/0245625 A1 | 10/2011 | Trovato et al. |
| 2011/0254922 A1 | 10/2011 | Schaerer et al. |
| 2012/0014608 A1 | 1/2012 | Watanabe |
| 2012/0068913 A1 | 3/2012 | Bar-zeev et al. |
| 2012/0078236 A1 | 3/2012 | Schoepp |
| 2012/0109151 A1 | 5/2012 | Maier-hein et al. |
| 2012/0143050 A1 | 6/2012 | Heigl |
| 2012/0155064 A1 | 6/2012 | Waters |
| 2012/0182605 A1 | 7/2012 | Hall et al. |
| 2012/0216411 A1 | 8/2012 | Wevers et al. |
| 2012/0289777 A1 | 11/2012 | Chopra et al. |
| 2012/0306850 A1 | 12/2012 | Balan et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0083009 A1 | 4/2013 | Geisner et al. |
| 2013/0106833 A1 | 5/2013 | Fun |
| 2013/0135734 A1 | 5/2013 | Shafer et al. |
| 2013/0190602 A1 | 7/2013 | Liao |
| 2013/0209953 A1 | 8/2013 | Arlinsky et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0249787 A1 | 9/2013 | Morimoto |
| 2013/0249945 A1 | 9/2013 | Kobayashi |
| 2013/0265623 A1 | 10/2013 | Sugiyama et al. |
| 2013/0267838 A1 | 10/2013 | Fronk et al. |
| 2013/0278635 A1 | 10/2013 | Maggiore |
| 2013/0300760 A1 | 11/2013 | Sugano et al. |
| 2013/0342571 A1 | 12/2013 | Kinnebrew et al. |
| 2014/0031668 A1 | 1/2014 | Mobasser et al. |
| 2014/0049629 A1* | 2/2014 | Siewerdsen ............ A61B 34/20 348/77 |
| 2014/0088402 A1 | 3/2014 | Xu |
| 2014/0088990 A1 | 3/2014 | Nawana et al. |
| 2014/0104505 A1 | 4/2014 | Koenig |
| 2014/0114173 A1 | 4/2014 | Bar-Tal et al. |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | Mccarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0300632 A1 | 10/2014 | Laor |
| 2014/0300967 A1 | 10/2014 | Tilleman et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1 | 11/2014 | Reiter |
| 2014/0340286 A1 | 11/2014 | Machida et al. |

(56) References Cited

U.S. PATENT DOCUMENTS

| | | |
|---|---|---|
| 2014/0361956 A1 | 12/2014 | Mikhailov et al. |
| 2015/0005772 A1 | 1/2015 | Anglin et al. |
| 2015/0018672 A1 | 1/2015 | Blumhofer et al. |
| 2015/0070347 A1 | 3/2015 | Hofmann et al. |
| 2015/0084990 A1 | 3/2015 | Labor |
| 2015/0150641 A1 | 6/2015 | Daon et al. |
| 2015/0182293 A1 | 7/2015 | Yang et al. |
| 2015/0209119 A1 | 7/2015 | Theodore et al. |
| 2015/0287188 A1 | 10/2015 | Gazit |
| 2015/0287236 A1 | 10/2015 | Winn |
| 2015/0297314 A1 | 10/2015 | Fowler et al. |
| 2015/0305828 A1 | 10/2015 | Park et al. |
| 2015/0310668 A1 | 10/2015 | Ellerbrock |
| 2015/0351863 A1 | 12/2015 | Plassky et al. |
| 2015/0366620 A1 | 12/2015 | Cameron et al. |
| 2016/0103318 A1 | 4/2016 | Du et al. |
| 2016/0125603 A1 | 5/2016 | Tanji |
| 2016/0143699 A1 | 5/2016 | Tanji |
| 2016/0153004 A1 | 6/2016 | Zhang |
| 2016/0175064 A1 | 6/2016 | Stenile et al. |
| 2016/0178910 A1 | 6/2016 | Gudicell et al. |
| 2016/0191887 A1 | 6/2016 | Casas |
| 2016/0223822 A1 | 8/2016 | Harrison et al. |
| 2016/0256223 A1 | 9/2016 | Haimer et al. |
| 2016/0302870 A1 | 10/2016 | Wilkinson et al. |
| 2016/0324580 A1 | 11/2016 | Esterberg |
| 2016/0324583 A1 | 11/2016 | Kheradpr et al. |
| 2016/0339337 A1 | 11/2016 | Ellsworth et al. |
| 2017/0027650 A1 | 2/2017 | Merck et al. |
| 2017/0068119 A1 | 3/2017 | Antaki |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0014119 A1 | 6/2017 | Capote et al. |
| 2017/0164919 A1 | 6/2017 | LaVallee et al. |
| 2017/0164920 A1 | 6/2017 | Lavallee et al. |
| 2017/0178375 A1* | 6/2017 | Benishti ............. G02B 27/0172 |
| 2017/0220224 A1 | 8/2017 | Kodali |
| 2017/0239015 A1 | 8/2017 | Sela et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0312032 A1 | 11/2017 | Amanatullah et al. |
| 2017/0348055 A1 | 12/2017 | Salcedo et al. |
| 2017/0348061 A1 | 12/2017 | Joshi et al. |
| 2017/0367766 A1 | 12/2017 | Mahfouz |
| 2017/0367771 A1 | 12/2017 | Tako et al. |
| 2017/0372477 A1 | 12/2017 | Penne |
| 2018/0003981 A1 | 1/2018 | Urey |
| 2018/0018791 A1 | 1/2018 | Guoyi |
| 2018/0028266 A1 | 2/2018 | Barnes et al. |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0078316 A1 | 3/2018 | Schaewe et al. |
| 2018/0082480 A1 | 3/2018 | White et al. |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0117150 A1 | 5/2018 | O'Dwyer |
| 2018/0133871 A1 | 5/2018 | Farmer |
| 2018/0153626 A1 | 6/2018 | Yang et al. |
| 2018/0185100 A1 | 7/2018 | Weinstein et al. |
| 2018/0193097 A1 | 7/2018 | McLachlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0311011 A1 | 11/2018 | Van Beek et al. |
| 2018/0317803 A1 | 11/2018 | Ben-Yishai et al. |
| 2018/0318035 A1 | 11/2018 | McLachlin et al. |
| 2019/0000372 A1 | 1/2019 | Gullotti et al. |
| 2019/0015163 A1 | 1/2019 | Abhari et al. |
| 2019/0038362 A1* | 2/2019 | Nash .................... H04N 13/366 |
| 2019/0038365 A1 | 2/2019 | Soper |
| 2019/0043238 A1 | 2/2019 | Benishti et al. |
| 2019/0046272 A1 | 2/2019 | Zoabi et al. |
| 2019/0046276 A1* | 2/2019 | Inglese ................ A61C 9/0046 |
| 2019/0053851 A1 | 2/2019 | Siemionow et al. |
| 2019/0069971 A1 | 3/2019 | Tripathi et al. |
| 2019/0080515 A1* | 3/2019 | Geri ...................... A61B 90/36 |
| 2019/0105116 A1 | 4/2019 | Johnson et al. |
| 2019/0130792 A1 | 5/2019 | Rios |
| 2019/0142519 A1 | 5/2019 | Siemionow et al. |
| 2019/0144443 A1 | 5/2019 | Jackson |
| 2019/0175228 A1 | 6/2019 | Elimelech et al. |
| 2019/0192230 A1 | 6/2019 | Siemionow et al. |
| 2019/0201106 A1 | 7/2019 | Siemionow et al. |
| 2019/0216537 A1 | 7/2019 | Eltorai |
| 2019/0254753 A1 | 8/2019 | Johnson |
| 2019/0273916 A1 | 9/2019 | Benishti et al. |
| 2019/0333480 A1 | 10/2019 | Lang |
| 2019/0369717 A1 | 12/2019 | Frielinghaus |
| 2019/0387351 A1 | 12/2019 | Lyren |
| 2020/0019364 A1 | 1/2020 | Pond |
| 2020/0020249 A1 | 1/2020 | Jarc et al. |
| 2020/0038112 A1 | 2/2020 | Amanatullah |
| 2020/0078100 A1 | 3/2020 | Weinstein et al. |
| 2020/0085511 A1 | 3/2020 | Oezbek et al. |
| 2020/0088997 A1 | 3/2020 | Lee |
| 2020/0159313 A1 | 3/2020 | Gibby et al. |
| 2020/0100847 A1 | 4/2020 | Siegler et al. |
| 2020/0117025 A1 | 4/2020 | Sauer |
| 2020/0129058 A1 | 4/2020 | Li |
| 2020/0129136 A1 | 4/2020 | Harding et al. |
| 2020/0129262 A1 | 4/2020 | Verard |
| 2020/0129264 A1 | 4/2020 | Onativia et al. |
| 2020/0133029 A1 | 4/2020 | Yonezawa |
| 2020/0138518 A1 | 5/2020 | Lang |
| 2020/0143594 A1 | 5/2020 | Lal et al. |
| 2020/0146546 A1 | 5/2020 | Chene |
| 2020/0151507 A1 | 5/2020 | Siemionow et al. |
| 2020/0156259 A1 | 5/2020 | Morales |
| 2020/0163723 A1 | 5/2020 | Wolf et al. |
| 2020/0163739 A1 | 5/2020 | Messinger et al. |
| 2020/0184638 A1 | 6/2020 | Meglan |
| 2020/0186786 A1 | 6/2020 | Gibby et al. |
| 2020/0188034 A1 | 6/2020 | Lequette et al. |
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent |
| 2020/0246074 A1 | 8/2020 | Lang |
| 2020/0246081 A1 | 8/2020 | Johnson et al. |
| 2020/0265273 A1 | 8/2020 | Wei |
| 2020/0275988 A1 | 9/2020 | Johnson |
| 2020/0305980 A1 | 10/2020 | Lang |
| 2020/0321099 A1 | 10/2020 | Holladay et al. |
| 2020/0323460 A1 | 10/2020 | Busza |
| 2020/0327721 A1 | 10/2020 | Siemionow et al. |
| 2020/0330179 A1 | 10/2020 | Ton |
| 2020/0337780 A1 | 10/2020 | Winkler |
| 2020/0341283 A1 | 10/2020 | McCracken |
| 2020/0352655 A1 | 11/2020 | Freese |
| 2020/0355927 A1 | 11/2020 | Marcellin-Dibon |
| 2020/0360091 A1 | 11/2020 | Murray et al. |
| 2020/0375666 A1 | 12/2020 | Murphy |
| 2020/0377493 A1 | 12/2020 | Heiser |
| 2020/0377956 A1 | 12/2020 | Vogelstein |
| 2020/0388075 A1 | 12/2020 | Kazanzides et al. |
| 2020/0389425 A1 | 12/2020 | Bhatia |
| 2020/0390503 A1 | 12/2020 | Casas et al. |
| 2020/0402647 A1 | 12/2020 | Domracheva |
| 2020/0410687 A1 | 12/2020 | Siemionow et al. |
| 2020/0413031 A1 | 12/2020 | Khani |
| 2021/0004956 A1 | 1/2021 | Book et al. |
| 2021/0009339 A1 | 1/2021 | Morrison et al. |
| 2021/0015583 A1 | 1/2021 | Avisar |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0029804 A1 | 1/2021 | Chang |
| 2021/0030374 A1 | 2/2021 | Takahashi |

(56) References Cited

U.S. PATENT DOCUMENTS

| | | |
|---|---|---|
| 2021/0030511 A1 | 2/2021 | Wolf et al. |
| 2021/0038339 A1 | 2/2021 | Yu |
| 2021/0065911 A1 | 3/2021 | Goel et al. |
| 2021/0077195 A1 | 3/2021 | Saeidi |
| 2021/0077210 A1 | 3/2021 | Itkowitz |
| 2021/0080751 A1 | 3/2021 | Lindsey |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quid et al. |
| 2021/0104055 A1 | 4/2021 | Ni et al. |
| 2021/0107923 A1 | 4/2021 | Jackson |
| 2021/0109349 A1 | 4/2021 | Schneider |
| 2021/0109373 A1 | 4/2021 | Loo |
| 2021/0110517 A1 | 4/2021 | Flohr |
| 2021/0113269 A1 | 4/2021 | Vilsmeier |
| 2021/0121238 A1 | 4/2021 | Palushi et al. |
| 2021/0137634 A1 | 5/2021 | Lang et al. |
| 2021/0141887 A1 | 5/2021 | Kim et al. |
| 2021/0150702 A1 | 5/2021 | Claessen |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing |
| 2021/0165207 A1 | 6/2021 | Peyman |
| 2021/0169504 A1 | 6/2021 | Brown |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0196404 A1 | 7/2021 | Wang |
| 2021/0223577 A1 | 7/2021 | Zheng |
| 2021/0227791 A1 | 7/2021 | De Oliveira Seixas |
| 2021/0235061 A1 | 7/2021 | Hegyi |
| 2021/0248822 A1 | 8/2021 | Choi |
| 2021/0282887 A1 | 9/2021 | Wiggermann |
| 2021/0290046 A1 | 9/2021 | Nazareth |
| 2021/0290336 A1 | 9/2021 | Wang |
| 2021/0290394 A1 | 9/2021 | Mahfouz |
| 2021/0295512 A1 | 9/2021 | Knoplioch |
| 2021/0298835 A1 | 9/2021 | Wang |
| 2021/0306599 A1 | 9/2021 | Pierce |
| 2021/0311322 A1 | 10/2021 | Belanger |
| 2021/0315636 A1 | 10/2021 | Akbarian |
| 2021/0315662 A1 | 10/2021 | Freeman et al. |
| 2021/0325684 A1 | 10/2021 | Ninan |
| 2021/0333561 A1 | 10/2021 | Oh |
| 2021/0346115 A1 | 11/2021 | Dulin et al. |
| 2021/0349677 A1 | 11/2021 | Baldev |
| 2021/0369226 A1 | 12/2021 | Siemionow et al. |
| 2021/0371413 A1 | 12/2021 | Thurston |
| 2021/0373333 A1 | 12/2021 | Moon |
| 2021/0373344 A1 | 12/2021 | Loyola |
| 2021/0378757 A1 | 12/2021 | Bay |
| 2021/0389590 A1 | 12/2021 | Freeman |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0079675 A1 | 3/2022 | Lang |
| 2022/0121041 A1 | 4/2022 | Hakim |
| 2022/0142730 A1 | 5/2022 | Wolf et al. |
| 2022/0155861 A1 | 5/2022 | Myung |
| 2022/0159227 A1 | 5/2022 | Casas |
| 2022/0179209 A1 | 6/2022 | Cherukuri |
| 2022/0192776 A1 | 6/2022 | Gibby et al. |
| 2022/0245400 A1 | 8/2022 | Siemionow et al. |
| 2022/0133484 A1 | 9/2022 | Lang |
| 2022/0287676 A1 | 9/2022 | Steines et al. |
| 2022/0295033 A1 | 9/2022 | Casas |

FOREIGN PATENT DOCUMENTS

| | | |
|---|---|---|
| CN | 101379412 B | 3/2009 |
| CN | 103106348 A | 5/2013 |
| CN | 111915696 A | 11/2020 |
| CN | 112489047 A | 3/2021 |
| CN | 112489047 B | 3/2021 |
| DE | 202004011567 U1 | 11/2004 |
| DE | 102014008153 A1 | 10/2014 |
| EP | 0933096 A2 | 8/1999 |
| EP | 1640750 A1 | 3/2006 |
| EP | 2134847 B1 | 6/2015 |
| EP | 2891966 B1 | 1/2017 |
| EP | 2654749 B1 | 5/2017 |
| EP | 3216416 A1 | 9/2017 |
| EP | 2032039 B1 | 10/2017 |
| EP | 2030193 B1 | 7/2018 |
| EP | 3034607 B1 | 3/2019 |
| EP | 2892558 B1 | 4/2019 |
| EP | 2635299 B1 | 7/2019 |
| EP | 3505050 A1 | 7/2019 |
| EP | 3224376 B1 | 8/2019 |
| EP | 2875149 B1 | 12/2019 |
| EP | 3206583 B1 | 9/2020 |
| EP | 2625845 B1 | 3/2021 |
| EP | 3076660 B1 | 4/2021 |
| EP | 3858280 A1 | 8/2021 |
| EP | 3593227 B1 | 9/2021 |
| EP | 3789965 B1 | 12/2021 |
| EP | 3634294 B1 | 1/2022 |
| EP | 3952331 A1 | 2/2022 |
| GB | 2507314 A | 4/2014 |
| KR | 20140120155 A | 10/2014 |
| WO | 03034705 A2 | 4/2003 |
| WO | 2007051304 A1 | 5/2007 |
| WO | 2007115826 A2 | 10/2007 |
| WO | 2008103383 A1 | 8/2008 |
| WO | 2010067267 A1 | 6/2010 |
| WO | WO2010074747 A1 | 7/2010 |
| WO | WO2012101286 A1 | 8/2012 |
| WO | 2013112554 A1 | 8/2013 |
| WO | 2014024188 A1 | 2/2014 |
| WO | 2014037953 A2 | 3/2014 |
| WO | WO2014037953 A2 | 3/2014 |
| WO | 2014113455 A1 | 7/2014 |
| WO | 2014125789 A1 | 8/2014 |
| WO | 2014167563 A1 | 10/2014 |
| WO | 2014174067 A1 | 10/2014 |
| WO | 2015058816 A1 | 4/2015 |
| WO | WO2015061752 A1 | 4/2015 |
| WO | WO2015109145 A1 | 7/2015 |
| WO | 2016151506 A1 | 9/2016 |
| WO | WO2007115826 A2 | 10/2017 |
| WO | 2018073452 A1 | 4/2018 |
| WO | WO2018200767 A1 | 4/2018 |
| WO | 2018206086 A1 | 11/2018 |
| WO | 2019195926 A1 | 10/2019 |
| WO | 2019211741 A1 | 11/2019 |
| WO | WO2019210353 A1 | 11/2019 |
| WO | 2020109903 A1 | 6/2020 |
| WO | 2020109904 A1 | 6/2020 |
| WO | 2021019369 A1 | 2/2021 |
| WO | WO2021017019 A1 | 2/2021 |
| WO | WO2021023574 A1 | 2/2021 |
| WO | WO2021046455 A1 | 3/2021 |
| WO | WO2021048158 A1 | 3/2021 |
| WO | WO2021021979 A2 | 4/2021 |
| WO | WO2021061459 A1 | 4/2021 |
| WO | WO2021062375 A1 | 4/2021 |
| WO | WO2021073743 A1 | 4/2021 |
| WO | WO2021087439 A1 | 5/2021 |
| WO | WO2021091980 A1 | 5/2021 |
| WO | 2021255627 A1 | 6/2021 |
| WO | WO2021112918 A1 | 6/2021 |
| WO | 2021130564 A1 | 7/2021 |
| WO | WO2021137752 A1 | 7/2021 |
| WO | WO2021141887 A1 | 7/2021 |
| WO | WO2021145584 A1 | 7/2021 |
| WO | WO2021154076 A1 | 8/2021 |

(56) References Cited

FOREIGN PATENT DOCUMENTS

| WO | WO2021183318 A2 | 12/2021 |
| WO | WO2021257897 A1 | 12/2021 |
| WO | WO2021258078 A1 | 12/2021 |
| WO | WO2022009233 A1 | 1/2022 |
| WO | 2022053923 A1 | 3/2022 |
| WO | 2022079565 A1 | 4/2022 |
| WO | 2023281395 A1 | 1/2023 |

OTHER PUBLICATIONS

International Application # PCT/IB2019/059770 search report dated Mar. 17, 2020.
International Application # PCT/IB2019/059771 search report dated Mar. 1, 2020.
U.S. Appl. No. 16/419,023 Third party submission dated Jan. 19, 2020.
Sagitov et al., "Comparing Fiducial Marker Systems in the Presence of Occlusion", International Conference on Mechanical, System and Control Engineering (ICMSC), pp. 1-6, 2017.
Liu et al., "Marker orientation in fiducial registration", Medical Imaging 2003: Image Processing, Proceedings of SPIE vol. 5032, pp. 1176-1185, 2003.
U.S. Appl. No. 16/419,023 office action dated Oct. 4, 2019.
Fingas., "Fraunhofer iPad app guides liver surgery through augmented reality", pp. 1-6, Aug. 22, 2013.
U.S. Appl. No. 16/419,023 Office Action dated Sep. 3, 2020.
U.S. Appl. No. 16/199,281 Office Action dated Jun. 11, 2020.
Liao et al., '3-D Augmented Reality for MRI-Guided Surgery Using Integral Videography Autostereoscopic Image Overlay', IEEE Transactions on Biomedical Engineering, vol. 57, No. 6, pp. 1476-1486, Feb. 17, 2010.
Hainich et al., "Near-Eye displays", Chapter 10 of Displays: Fundamentals and Applications, CRC press, pp. 439-504, Jul. 5, 2011.
Brainlab—Image Registration Options Enhanced Visualization Leveraging More Data, pp. 1-4, Feb. 2019.
Lumus Ltd., "DK-32 See-through Wearable Display Development Kit", Rehovot, Israel, 2 pages, Dec. 24, 2013.
International Application # PCT/IB2020/056893 Search Report dated Nov. 9, 2020.
International Application # PCT/IB2020/060017 Search Report dated Jan. 7, 2021.
Elimelech et al., U.S. Appl. No. 16/724,297, filed Dec. 22, 2019.
U.S. Appl. No. 16/724,297 Office Action dated Jan. 26, 2021.
JP Application # 2021525186 Office Action dated Dec. 1, 2021.
EP Application # 19796580.9 Search Report dated Dec. 20, 2021.
International Application # PCT/IB2021/058088 Search Report dated Dec. 20, 2021.
International Application # PCT/IB2021/055242 Search Report dated Oct. 7, 2021.
U.S. Appl. No. 16/724,297 Office Action dated Nov. 4, 2021.
CN Application # 2019800757525 Office Action dated Mar. 1, 2022.
U.S. Appl. No. 16/419,023 Office Action dated Mar. 1, 2022.
U.S. Appl. No. 16/524,258 Office Action dated Apr. 11, 2022.
EP Application # 16767845.7 Office Action dated Apr. 29, 2022.
Lorensen et al., "Marching Cubes: A High Resolution 3D Surface Construction Algorithm," ACM SIGGRAPH '87, Computer Graphics, vol. 21, No. 4, pp. 163-169, Jul. 1987.
Wikipedia, "Marching Cubes," pp. 1-4, last edited Sep. 4, 2021.
Milletari et al., "V-Net: fully Convolutional Neural Networks for Volumetric Medical Image Segmentation," arXiv:1606.04797v1, pp. 1-11, Jun. 15, 2016.
EP Application # 19891059.8 Search Report dated Jul. 27, 2022.
EP Application # 19890849.3 Search Report dated Jul. 27, 2022.
U.S. Appl. No. 16/419,023 Office Action dated Sep. 1, 2022.
U.S. Appl. No. 16/524,258 Office Action dated Oct. 24, 2022.
Mitrasinovic et al., "Clinical and surgical applications of smart glasses", pp. 381-401, Technology and Health Care, issue 23, year 2015.
Martin-Gonzalez et al., "Head-mounted virtual loupe with sight-based activation for surgical applications", IEEE symposium on mixed and augmented reality, pp. 207-208, Oct. 19-22, 2009.
Figl et al., "A fully automated calibration method for an optical see-through head-mounted operating microscope with variable zoom and focus", pp. 1492-1499, IEEE transactions on medical imaging, vol. 24, No. 11, Nov. 2005.
Medithinq Co. Ltd., "Metascope: world's first wearable scope", pp. 1-7, Jan. 2023.
Martin-Gonzalez et al., "Sight-based magnification system for surgical applications", pp. 26-30, Conference proceedings of Bildverarbeitung für die Medizin, year 2010.
Burstrom et al., "Frameless patient tracking with adhesive optical skin markers for augmented reality surgical navigation in spine surgery", Spine, vol. 45, No. 22, pp. 1598-1604, year 2020.
Suenaga et al., "Vision-based markerless registration using stereo vision and an augmented reality surgical navigation system: a pilot study", BMC Medical Imaging, pp. 1-11, year 2015.
Mayfield Clinic, "Spinal Fusion: Lateral Lumbar Interbody Fusion (LLIF)", pp. 1-6, Jan. 2021.
Qian et al., "AR-Loupe: Magnified Augmented Reality by Combining an Optical See-Through Head-Mounted Display and a Loupe", pp. 2550-2562, IEEE Transactions on Visualization and Computer Graphics, vol. 28, No. 7, Jul. 2022.
Kazanzides et al., "Systems and Methods for Augmented Reality Magnifying Loupe", case ID 15944, pp. 1-2, Nov. 26, 2020.
Zhang et al., "Medical Volume Rendering Techniques," Independent Research, Spring 2014, arXiv:1802.07710v1, pp. 1-33, Feb. 21, 2018.
Van Ooijen et al., "Noninvasive Coronary Imaging Using Electron Beam CT: Surface Rendering Versus Volume Rendering," Computers in Radiology, AJR, vol. 180, pp. 223-226, Jan. 2003.
Webster (ed.), "Structured Light Techniques and Applications," Wiley Encyclopedia of Electrical and Electronics Engineering, pp. 1-24, year 2016.
Liberadzki et al., "Structured-Light-Based System for Shape Measurement of the Human Body in Motion," Sensors, vol. 18, pp. 1-19, year 2018.
Romero, "Volume Ray Casting Techniques and Applications Using General Purpose Computations on Graphics Processing Units," Thesis/Dissertation Collections, Rochester Institute of Technology, RIT Scholar Works, pp. 1-140, Jun. 2009.
International Application PCT/IB2022/056986 filed Jul. 28, 2022.
International Application PCT/IB2022/057733 filed Aug. 18, 2022.
International Application PCT/IB2022/057735 filed Aug. 18, 2022.
International Application PCT/IB2022/057736 filed Aug. 18, 2022.
International Application PCT/IB2022/057965 filed Aug. 25, 2022.
International Application PCT/IB2022/059030 filed Sep. 23, 2022.
Gera et al., U.S. Appl. No. 17/388,064, filed Jul. 29, 2021.
International Application PCT/IB2022/057965 Search Report dated Dec. 15, 2022.
U.S. Appl. No. 16/524,258 Office Action dated Jan. 24, 2023.
International Application PCT/IB2022/057733 Search Report dated Jan. 26, 2023.
European Application 22203956.2 Search Report dated Feb. 9, 2023.
International Application PCT/IB2022/059030 Search report dated Feb. 28, 2023.
U.S. Appl. No. 16/419,023 Office Action dated Jul. 22, 2021.

* cited by examiner

TRACKING SYSTEM FOR IMAGE-GUIDED SURGERY

FIELD OF EMBODIMENTS OF THE INVENTION

The present invention relates to generally to an augmented reality system, and specifically to a tracking system for an augmented reality system that is used to perform image-guided surgery.

BACKGROUND

A head-mounted display is sometimes used as part of an augmented reality system. The display is used to generate an augmented reality scene, in which a scene that is being viewed by a user of the head-mounted display is altered, typically by being augmented or supplemented. The alteration is computer generated, and typically involves presenting real-time video, and/or non-real-time images, to the user while the user is gazing at the scene.

In some cases, an augmented reality system is used for performing image-guided surgery, as part of a medical procedure. For example, a computer-generated image may be presented to a healthcare professional who is performing the procedure. The image may be presented on a head-mounted display such that the image is aligned with an anatomical portion of a patient who is undergoing the procedure. Although some misalignment of the image with the patient's body may be acceptable, for satisfactory presentation of the images the misalignment may typically not be more than about 2-3 mm. In order to account for such a limit on the misalignment of the patient's anatomy with the presented images, the position of the patient's body or a portion thereof is typically tracked.

In some cases, an image of a tool that is used to perform the procedure is incorporated into the image that is displayed on the head-mounted display. In order to incorporate an image of the tool into the image, in a manner in which the position of the tool with respect to the image and/or the patient's anatomy is accurately reflected, the position of the tool or a portion thereof is typically tracked.

Triangulation techniques are commonly employed for tracking positions of a patient's body and/or a tool. In such techniques, a plurality of imaging devices, which are disposed at known locations with respect to each other, are used to detect a feature (such as a marker) on the patient's body, and/or on the tool. The location of the feature is then derived, using a combination of the known locations of the imaging devices, as well as the location of the feature as detected by each of the imaging devices.

SUMMARY OF EMBODIMENTS

In accordance with some applications of the present invention, a first healthcare professional (e.g., a surgeon performing a procedure) wears a first head-mounted device. Typically, the head-mounted device includes one or more head-mounted displays. For some applications, the head-mounted displays are generally similar to those described in U.S. Pat. No. 9,928,629 to Benishti, which is incorporated herein by reference. For example, the head-mounted displays may include a combiner that is controlled by a computer processor, such as to display an augmented reality image to the healthcare professional. For some applications, the image is presented on the head-mounted display such that (a) a computer-generated image is projected onto a first portion of the display, and (b) the computer-generated image is aligned with an anatomical portion of a patient who is undergoing the procedure, with the anatomical portion of a patient visible through a second portion of the display. Typically, the computer-generated image includes a virtual image of the tool overlaid upon a virtual image of the patient's anatomy. For some applications, a portion of the tool that would not otherwise be visible to the healthcare professional (for example, by virtue of being hidden by the patient's anatomy) is included in the computer-generated image.

Typically, the head-mounted device includes a tracking device that is configured to facilitate determination of the location and orientation of the head-mounted device with respect to a portion of the patient's body (e.g., the patient's back), and/or the position and orientation of the tool with respect to the patient's body. For example, the tracking device may include an image-capturing device, such as a camera, that is configured to image a patient marker and/or a tool marker. Typically, the patient marker is configured to provide data that is sufficient for the computer processor to determine the location and orientation of the head-mounted device with respect to the portion of the patient's body using data collected from a single tracking device that is disposed on the head-mounted display. For example, the patient marker may include an array of elements that is visible to the tracking device of the head-mounted device, and that is configured such that at any location and orientation of the head-mounted device with respect to the patient marker, the array of elements has an appearance that is unique to that location and orientation. In this manner, the computer processor is able to determine the location and orientation of the head-mounted device with respect to the portion of the patient's body without requiring the use of triangulation techniques. Typically, a single camera is used in the tracking device of the head-mounted device. For some applications, the camera is a high-speed camera. For example, the camera may acquire more than 50 frames per second.

Typically, in order to generate the augmented reality image upon the head-mounted display, a computer processor determines the location and orientation of the head-mounted device with respect to a portion of the patient's body (e.g., the patient's back), and/or the position and orientation of the tool with respect to the portion of the patient's body. As described hereinabove, in general, the patient marker is configured to provide data that is sufficient for the computer processor to determine the location and orientation of the head-mounted device with respect to the portion of the patient's body using data collected from a single tracking device that is disposed on the head-mounted device. However, for some applications, at least under certain conditions, the computer processor is configured to incorporate tracking data that is received from at least one additional tracking device (i.e., a tracking device in addition to the tracking device that is included in the head-mounted device of the first healthcare professional), in order to generate the image upon the head-mounted display of the first healthcare professional.

For some such applications, the computer processor is configured to incorporate the additional data in cases in which the first tracking device that is included in the head-mounted device of the first healthcare professional loses its line of sight with the patient marker and/or the tool marker and/or portions thereof. For example, the computer processor may be configured to receive data from a tracking device of an additional head-mounted device that is configured to be worn by an additional healthcare professional who is present in the procedure (e.g., an accompanying surgeon or a nurse). Typically, the additional head-mounted device is generally similar to the first head-mounted device, and the tracking device of the additional head-mounted device is generally similar to that of the first head-mounted device. For some applications, when at least a portion of the patient marker and a portion of the tool (e.g., the tool marker) are both within the line of sight of the first tracking device, the computer processor generates an augmented reality image upon the head-mounted display, based upon data received from first tracking device and without using data received from the additional tracking device. When at least the portion of the patient marker and the portion of the tool are not both within the line of sight of the first tracking device, the computer processor generates an augmented reality image upon the first head-mounted display, at least partially based upon data received from the additional tracking device.

There is therefore provided, in accordance with some applications of the present invention, a method for use with a tool configured to be placed within a portion of a body of a patient, the method including:

tracking at least a portion of the tool and a patient marker that is placed upon the patient's body from a first line of sight, using a first tracking device that is disposed upon a first head-mounted device that is worn by a first person, the first head-mounted device including a first head-mounted display;

tracking at least the portion of the tool and the patient marker, from a second line of sight, using a second tracking device; and using at least one computer processor:
when at least a portion of the patient marker and the portion of the tool are both within the first line of sight, generating an augmented reality image upon the first head-mounted display based upon data received from the first tracking device and without using data from the second tracking device, the augmented reality image including (a) a virtual image of the tool and anatomy of the patient, overlaid upon (b) the patient's body; and
when at least the portion of the patient marker and the portion of the tool are not both within the first line of sight, generating a virtual image of the tool and anatomy of the patient upon the first head-mounted display, at least partially based upon data received from the second tracking device.

In some applications, tracking the portion of the tool includes tracking a tool marker. In some applications, tracking at least the portion of the tool and the patient marker, from the second line of sight, using the second tracking device, includes tracking at least the portion of the tool and the patient marker from the second line of sight, using a second tracking device that is disposed in a stationary position. In some applications, tracking at least the portion of the tool and the patient marker using the first tracking device includes tracking at least the portion of the tool and the patient marker using a first camera, and tracking at least the portion of the tool and the patient marker using the second tracking device includes tracking at least the portion of the tool and the patient marker using a second camera.

In some applications, generating the virtual image of the tool and anatomy of the patient upon the first head-mounted display, at least partially based upon data received from the second tracking device includes:

in response to the portion of the patient marker being within the first line of sight, and the portion of the tool not being within the first line of sight:
determining a position of the tool with respect to the subject's anatomy using data received from the second tracking device;
generating the virtual image of the tool and anatomy of the patient upon the first head-mounted display, based upon the determined position of the tool with respect to the subject's anatomy;
determining a position of the patient's body with respect to the first head-mounted device based upon data received from the first tracking device; and
overlaying the virtual image upon the patient's body, based upon the determined position of the patient's body with respect to the first head-mounted device.

In some applications, generating the virtual image of the tool and anatomy of the patient upon the first head-mounted display, at least partially based upon data received from the second tracking device includes:

in response to the portion of the tool being within the first line of sight, and the portion of the patient marker not being within the first line of sight:
determining a position of the tool with respect to the subject's anatomy using data received from the second tracking device;
generating the virtual image of the tool and anatomy of the patient upon the first head-mounted display, based upon the determined position of the tool with respect to the subject's anatomy.

In some applications, generating the virtual image of the tool and anatomy of the patient upon the first head-mounted display further includes overlaying the virtual image upon the patient's body, based upon a position of the patient's body with respect to the first head-mounted device as determined based upon data received from the first tracking device at a time when the portion of the patient marker was within the first line of sight.

In some applications, overlaying the virtual image upon the patient's body includes tracking movements of the head-mounted device between the time when the portion of the patient marker was within the first line of sight and the portion of the patient marker not being within the first line of sight, using an inertial-measurement unit disposed upon the first head-mounted device.

In some applications, generating the virtual image of the tool and anatomy of the patient upon the first head-mounted display, at least partially based upon data received from the second tracking device includes:

in response to the portion of the tool and the portion of the patient marker both not being within the first line of sight:
determining a position of the tool with respect to the subject's anatomy using data received from the second tracking device;
generating the virtual image of the tool and anatomy of the patient upon the first head-mounted display, based upon the determined position of the tool with respect to the subject's anatomy.

In some applications, generating the virtual image of the tool and anatomy of the patient upon the first head-mounted display further includes overlaying the virtual image upon the patient's body, based upon a position of the patient's body with respect to the first head-mounted device as determined based upon data received from the first tracking device at a time when the portion of the patient marker was within the first line of sight. In some applications, overlaying the virtual image upon the patient's body includes tracking movements of the head-mounted device between the time when the portion of the patient marker was within the first line of sight and the portion of the patient marker not being within the first line of sight, using an inertial-measurement unit disposed upon the first head-mounted device.

In some applications, tracking at least the portion of the tool and the patient marker, from the second line of sight, using the second tracking device, includes tracking at least the portion of the tool and the patient marker from the second line of sight, using a second tracking device that is disposed upon a second head-mounted device that is worn by a second person. In some applications, the second head-mounted device includes a second head-mounted display, the method further including generating a further augmented-reality image upon the second head-mounted display.

There is further provided, in accordance with some applications of the present invention, apparatus for use with a tool configured to be placed within a portion of a body of a patient, the apparatus including:
 a patient marker configured to be placed upon the patient's body;
 a first head-mounted device including a first head-mounted display, and a first tracking device that is configured to track at least a portion of the tool and the patient marker from a first line of sight;
 a second tracking device that is configured to track at least the portion of the tool and the patient marker from a second line of sight; and
 at least one computer processor configured:
  when at least a portion of the patient marker and the portion of the tool are both within the first line of sight, to generate an augmented reality image upon the first head-mounted display, based upon data received from the first tracking device and without using data from the second tracking device, the augmented reality image including (a) a virtual image of the tool and anatomy of the patient, overlaid upon (b) the patient's body; and
  when at least the portion of the patient marker and the portion of the tool are not both within the first line of sight, to generate a virtual image of the tool and anatomy of the patient upon the first head-mounted display, at least partially based upon data received from the second tracking device.

There is further provided, in accordance with some applications of the present invention, a method for use with a tool configured to be placed within a portion of a body of a patient, the method including:
 tracking at least a portion of the tool and a patient marker that is placed upon the patient's body from a first line of sight, using a first tracking device that is disposed upon a first head-mounted device that is worn by a first person, the first head-mounted device including a first head-mounted display;
 tracking at least the portion of the tool and the patient marker from a second line of sight, using a second tracking device that is disposed upon a second head-mounted device that is worn by a second person; and
 using at least one computer processor, generating an augmented reality image upon the first head-mounted display, based upon data received from the first tracking device in combination with data received from the second tracking device, the augmented reality image including (a) a virtual image of the tool and anatomy of the patient, overlaid upon (b) the patient's body.

In some applications, tracking the portion of the tool includes tracking a tool marker. In some applications, the second head-mounted device includes a second head-mounted display, the method further including generating a further augmented-reality image upon the second head-mounted display. In some applications, tracking at least the portion of the tool and the patient marker using the first tracking device includes tracking at least the portion of the tool and the patient marker using a first camera, and tracking at least the portion of the tool and the patient marker using the second tracking device includes tracking at least the portion of the tool and the patient marker using a second camera.

In some applications, generating the augmented reality image upon the first head-mounted display includes:
 determining a position of the tool with respect to the subject's anatomy using data received from the first tracking device in combination with data received from the second tracking device;
 generating the virtual image of the tool and anatomy of the patient upon the first head-mounted display, based upon the determined position of the tool with respect to the subject's anatomy;
 determining a position of the patient's body with respect to the first head-mounted device based upon data received from the first tracking device; and
 overlaying the virtual image upon the patient's body, based upon the determined position of the patient's body with respect to the first head-mounted device.

There is further provided, in accordance with some applications of the present invention, apparatus for use with a tool configured to be placed within a portion of a body of a patient, the apparatus including:
 a patient marker configured to be placed upon the patient's body;
 a first head-mounted device configured to be worn by a first person, the first head-mounted device including a first head-mounted display, and a first tracking device that is configured to track at least a portion of the tool and the patient marker from a first line of sight;
 a second head-mounted device configured to be worn by a second person, the second head-mounted device including a second tracking device that is configured to track at least a portion of the tool and the patient marker from a second line of sight; and
 at least one computer processor configured to generate an augmented reality image upon the first head-mounted display, based upon data received from the first tracking device in combination with data received from the second tracking device, the augmented reality image including (a) a virtual image of the tool and anatomy of the patient, overlaid upon (b) the patient's body.

The present invention will be more fully understood from the following detailed description of applications thereof, taken together with the drawings, in which:

DETAILED DESCRIPTION OF EMBODIMENTS

Figure 1:
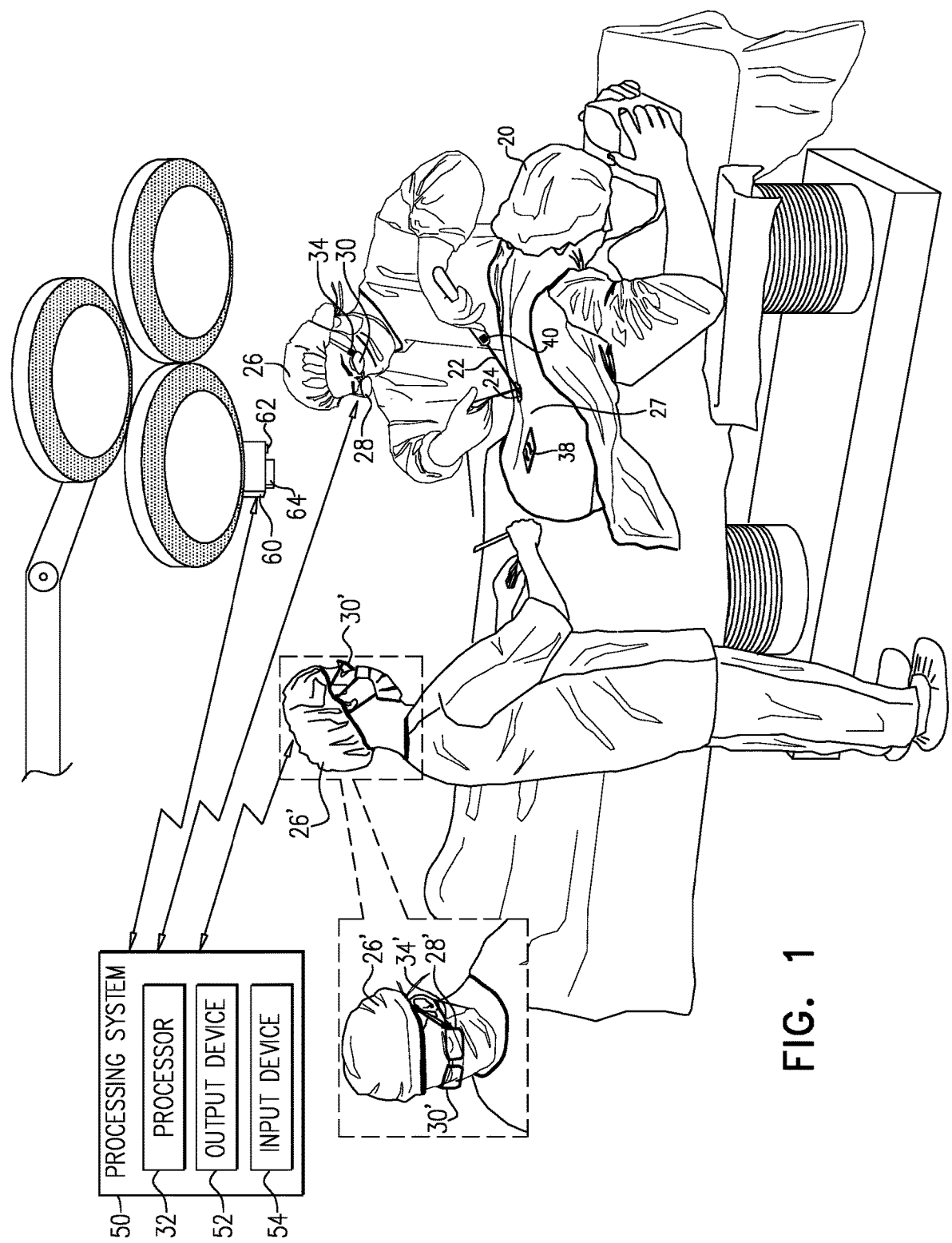
FIG. 1 is a schematic illustration of image-guided surgery being performed upon a patient, in accordance with some applications of the present invention.
Figure 2:
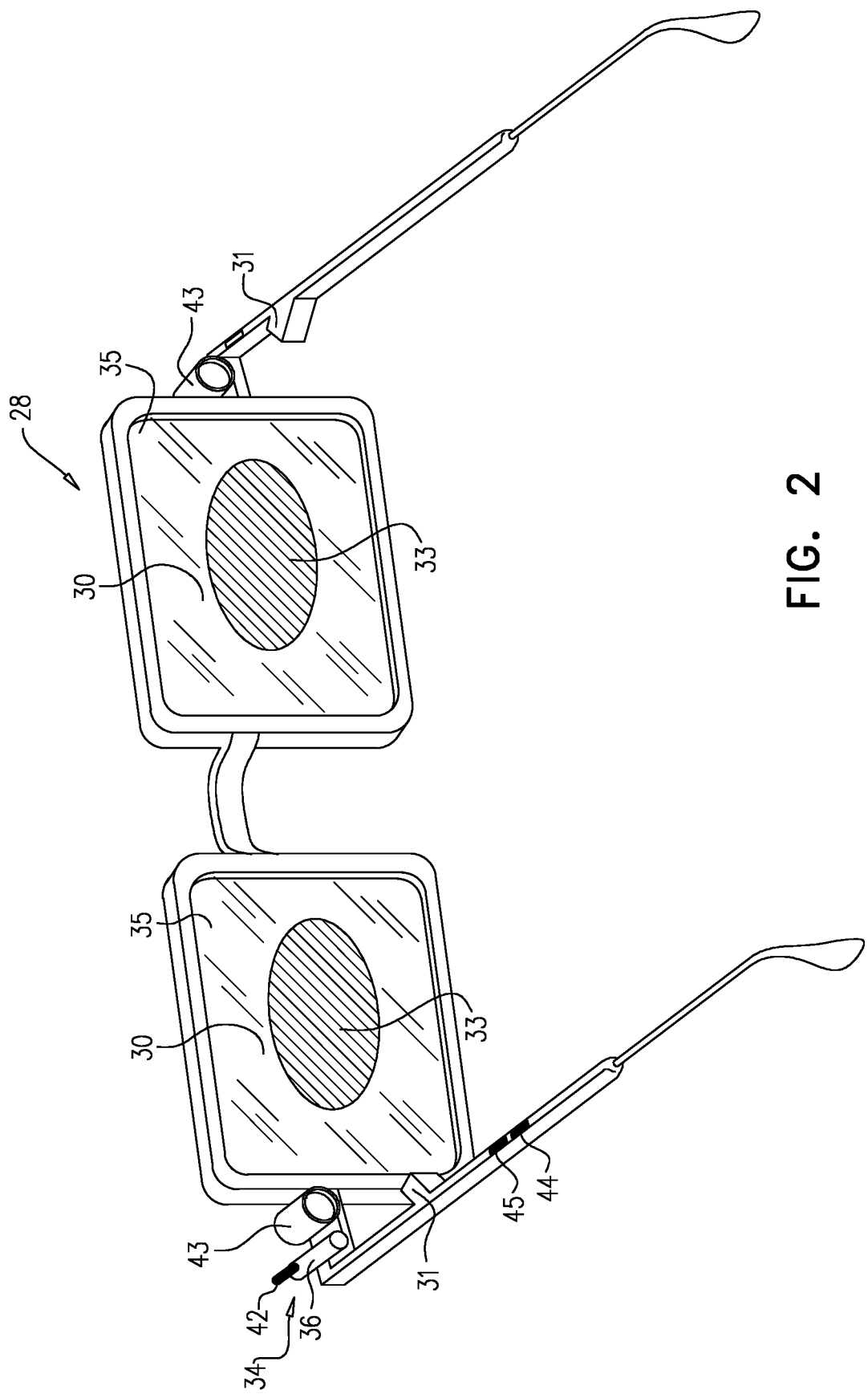
FIG. 2 is a schematic illustration of a head-mounted device, in accordance with some applications of the present invention.

Reference is now made to FIG. 1, which is a schematic illustration of a medical procedure that incorporates image-guided surgery being performed upon a patient 20, in accordance with some applications of the present invention. In the medical procedure shown in FIG. 1, a tool 22 is used to perform an action with respect to the patient's back, the tool being inserted via an incision 24 on the patient's back 27. However, the apparatus and techniques described herein may be used in any surgical procedure that is performed upon a patient's body, mutatis mutandis. Reference is also made to FIG. 2, which is a schematic illustration of a head-mounted device 28, in accordance with some applications of the present invention.

For some applications, a first healthcare professional 26 (e.g., a surgeon performing the procedure) wears a first head-mounted device 28. Typically, the head-mounted device includes one or more head-mounted displays 30. For some applications, the head-mounted displays are generally similar to those described in U.S. Pat. No. 9,928,629 to Benishti, which is incorporated herein by reference. For example, the head-mounted displays may include a combiner that is controlled by a computer processor (e.g., computer processor 32 and/or computer processor 45 described hereinbelow), such as to display an augmented reality image to the healthcare professional. For some applications, the image is presented on head-mounted display 30 such that (a) a computer-generated image is projected onto a first portion 33 of the display by projector 31, and (b) the computer-generated image is aligned with an anatomical portion of a patient who is undergoing the procedure, with the anatomical portion of a patient being visible through a second portion 35 of the display. Typically, the computer-generated image includes a virtual image of the tool overlaid upon a virtual image of the patient's anatomy. For some applications, a portion of the tool that would not otherwise be visible to the healthcare professional (for example, by virtue of being hidden by the patient's anatomy) is included in the computer-generated image.

Although some misalignment of the image with the patient's body may be acceptable, for satisfactory presentation of the images the misalignment may typically not be more than about 2-3 mm. In order to account for such a limit on the misalignment of the patient's anatomy with the presented images, the position of the patient's body, or a portion thereof, with respect to the head-mounted device is typically tracked. In some cases, an image of a tool that is used to perform the procedure is incorporated into the image that is displayed on the head-mounted display. In order to incorporate an image of the tool into the image, in a manner in which the position of the tool with respect to the patient's anatomy is accurately reflected, the position of the tool or a portion thereof (e.g., the tool marker) is typically tracked. It is typically desirable to determine the location of the tool with respect to the patient's body such that errors in the determined location of the tool with respect to the patient's body are less than 2 mm.

Typically, head-mounted device 28 includes a tracking device 34 that is configured to facilitate determination of the location and orientation of head-mounted device 28 with respect to a portion of the patient's body (e.g., the patient's back) and/or with respect to tool 22, and/or the position and orientation of the tool with respect to the portion of the patient's body. For example, the tracking device may include an image-capturing device 36, such as a camera, that is configured to image a patient marker 38 and/or a tool marker 40. Typically, a single camera is used in the tracking device of the head-mounted device. For some applications, the camera is a high-speed camera. For example, the camera may acquire more than 50 frames per second.

For some applications, tracking device 34 includes a light source 42, which is mounted on the head-mounted device. The light source is typically configured to irradiate the patient marker and/or the tool marker, such that light reflects from the markers toward the camera. For some applications, image-capturing device 36 is a monochrome camera that includes a filter that is configured to only allow light to pass through that is of a similar wavelength to the light that is generated by the light source. For example, the light source may be an infrared light source (for example, a light source that generates light at a wavelength of between 700 nm and 1000 nm (e.g., between 700 nm and 800 nm)), and the camera may include a corresponding infrared filter. For some applications, an inertial-measurement unit 44 (e.g., an inertial-measurement unit configured to measure in 6 degrees-of-freedom) is disposed on the head-mounted device, as described in further detail hereinbelow. For some applications, the head-mounted device includes additional cameras 43, which are configured to capture images of scenes in the visible spectrum, as described in U.S. Pat. No. 9,928,629 to Benishti, which is incorporated herein by reference. For some applications, head-mounted device 28 includes additional components, for example, as described in U.S. Pat. No. 9,928,629 to Benishti, which is incorporated herein by reference.

Typically, in order to generate an augmented reality image upon display 30, a computer processor determines the location and orientation of head-mounted device 28 with respect to a portion of the patient's body (e.g., the patient's back), and/or the position and orientation of the tool with respect to the patient's body. For example, a computer processor 45 that is integrated within the head-mounted device may perform the aforementioned functionalities. Alternatively or additionally, computer processor 32, which is disposed externally to the head-mounted device and is typically in wireless communication with the head-mounted device may be used to perform these functionalities. Computer processor 32 typically comprises a portion of a processing system 50 that is used with the head-mounted device in order to facilitate the image-guided surgery. For some applications, the processing system additionally includes an output device 52 (e.g., a display, such as a monitor) for outputting information to an operator of the system, and/or an input device 54 (such as a pointing device, a keyboard, a mouse, etc.) configured to allow the operator to input data into the system. In general, in the context of the present application, when a computer processor is described as performing certain steps, these steps may be performed by external computer processor 32, and/or computer processor 45 that is integrated within the head-mounted device.

For some applications, the patient marker and/or the tool marker includes reflective elements that are configured to reflect light that is generated by light source 42. For some such applications, the location and orientation of a portion of the subject's body (e.g., the subject's back) with respect to the head-mounted device is tracked, by directing light from light source 42 toward a region of interest in which the patient marker is disposed. Alternatively or additionally, the location and orientation of the tool with respect to the portion of the subject's body, is tracked by directing light from light source 42 toward a region of interest in which the patient marker and/or the tool marker is disposed. Typically, image-capturing device 36 is disposed upon the head-mounted device in close proximity to the light source, such that the image-capturing device is configured to capture light that is retro-reflected from the patient marker and/or the tool marker. As described hereinabove, for some applications, the image-capturing device is a monochrome camera that includes a filter that is configured to only allow light to pass through that is of a similar wavelength to the light that is generated by the light source. For such applications, the camera typically receives a grayscale image showing the reflective elements of the tool marker and/or the patient marker. Typically, the computer processor determines the location of a portion of the subject's body (e.g., the subject's back) with respect to the head-mounted device by analyzing the images acquired by the image-capturing device. Further typically, the computer processor determines the location and orientation of the tool with respect to the portion of the subject's body, by analyzing the images acquired by the image-capturing device.

It is noted that the above-described technique for tracking the patient marker and/or the tool marker is presented by way of example, and that for some applications, alternative techniques are used for tracking the patient marker and/or the tool marker. For example, the patient marker and/or the tool marker may include light-absorbing elements, and/or light-generating elements, and the image-capturing device may be configured to track the patient marker and/or the tool marker by detecting these elements. Alternatively or additionally, a different type of detector may be used for tracking the patient marker and/or the tool marker.

Typically, the patient marker is configured to provide data that is sufficient for the computer processor to determine the location and orientation of the head-mounted device with respect to the portion of the patient's body using data collected from a single tracking device that is disposed on the head-mounted display. For example, the patient marker may include an array of elements that is visible to the tracking device of the head-mounted device, and that is configured such that at any location and orientation of the head-mounted device with respect to the patient marker, the array of elements has an appearance that is unique to that location and orientation. In this manner, the computer processor is able to determine the location and orientation of the head-mounted device with respect to the portion of the patient's body without requiring the use of triangulation techniques.

As described in the above paragraph, in general, the patient marker is configured to provide data that is sufficient for the computer processor to determine the location and orientation of the head-mounted device with respect to the portion of the patient's body using data collected from a single tracking device that is disposed on the head-mounted display. However, for some applications, at least under certain circumstances, the computer processor is configured to incorporate tracking data that is received from an additional tracking device (i.e., an additional tracking device to first tracking device 34), in order to generate the image upon head-mounted display 30 of first head-mounted device 28 of first healthcare professional 26.

For some such applications, the computer processor is configured to incorporate the additional data in cases in which tracking device 34 loses its line of sight with the patient marker and/or the tool marker and/or portions thereof. An example of this is shown in FIG. 1, which shows that the right hand of first healthcare professional 26 is blocking the line of sight of his/her tracking device 34 with respect to patient marker 38. For some applications, in such cases, the computer processor is configured to receive data from a tracking device 34' of an additional head-mounted device 28' that is configured to be worn by an additional healthcare professional 26' who is present in the procedure (e.g., an accompanying surgeon, or a nurse), e.g., as shown in FIG. 1. Typically, the additional head-mounted device 28' is generally similar to the first head-mounted device 28, and the tracking device 34' of the additional head-mounted device is generally similar to that of the first head-mounted device. For some applications, when at least a portion of the patient marker and a portion of the tool (e.g., the tool marker) are both within the line of sight of the first tracking device 34, the computer processor generates an augmented reality image upon the head-mounted display 30, based upon data received from first tracking device 34 and without using data received from tracking device 34'. When at least the portion of the patient marker and the portion of the tool are not both within the line of sight of first tracking device 34, the computer processor generates an augmented reality image upon head-mounted display 30, at least partially based upon data received from second tracking device 34'.

Alternatively or additionally, a tracking device 60, which is not mounted on a head-mounted device, is disposed in the operating room. Typically, tracking device 60 is disposed in a stationary position within the operating room. For example, tracking device 60 may be ceiling-mounted, wall-mounted, and/or disposed on a stand, such as a tripod. For some applications, tracking device 60 includes a light source 62 and an image-capturing device 64, which function in a generally similar manner to that described hereinabove with reference to light source 42 and image-capturing device 36.

Figure 3A:
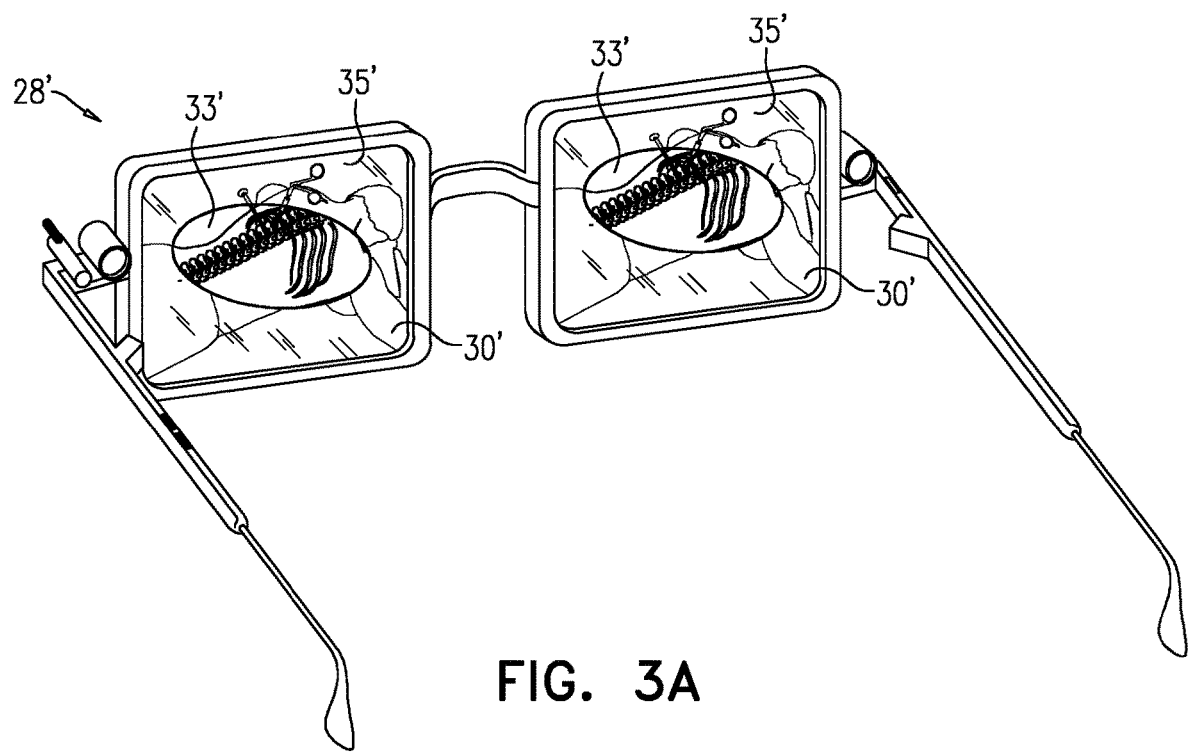
FIGS. 3A and 3B are schematic illustrations of examples of displays of head-mounted devices as worn by respective healthcare professionals, in accordance with some applications of the present invention.
Figure 3B:
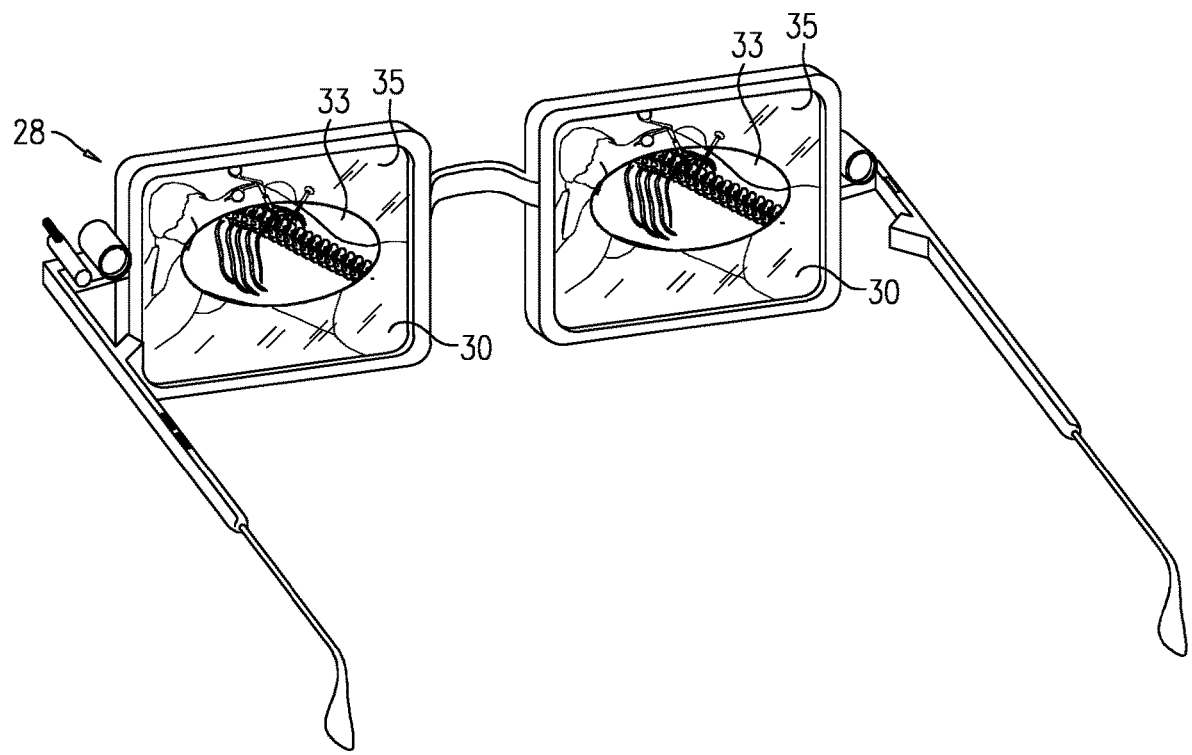

Reference is now made to FIGS. 3A and 3B, which are schematic illustration of examples of displays 30', 30 of head-mounted devices 28', 28 as worn by respective healthcare professionals 26', 26, in accordance with some applications of the present invention. FIG. 3A shows an example of displays 30' of second healthcare professional 26', who is shown on the right side of the patient in FIG. 1, and FIG. 3B shows an example of displays 30 of first healthcare professional 26, who is shown on the left side of the patient in FIG. 1. Typically, the image that is generated upon each of head-mounted displays 30 and head-mounted displays 30' is an augmented-reality view showing virtual patient anatomy aligned with the actual patient anatomy and a virtual tool aligned with the virtual anatomy. As described hereinabove, for some applications, the virtual tool and virtual anatomy are displayed upon a first portion 33 of head-mounted display 30, 30', and the actual patient anatomy is visible through a second portion 35 of head-mounted display 30, 30'. For some applications, the computer processor is configured to generate such a view both in 2D and 3D. In order to generate such a view, it is typically necessary to track the location and orientation of the head-mounted device relative to the patient, in order to correctly align the virtual anatomy with the actual patient anatomy. FIGS. 3A and 3B show how the respective head-mounted displays typically appear, when tracking devices 34 of each of the healthcare professionals has a clear line of sight of the patient marker.

Figure 4A:
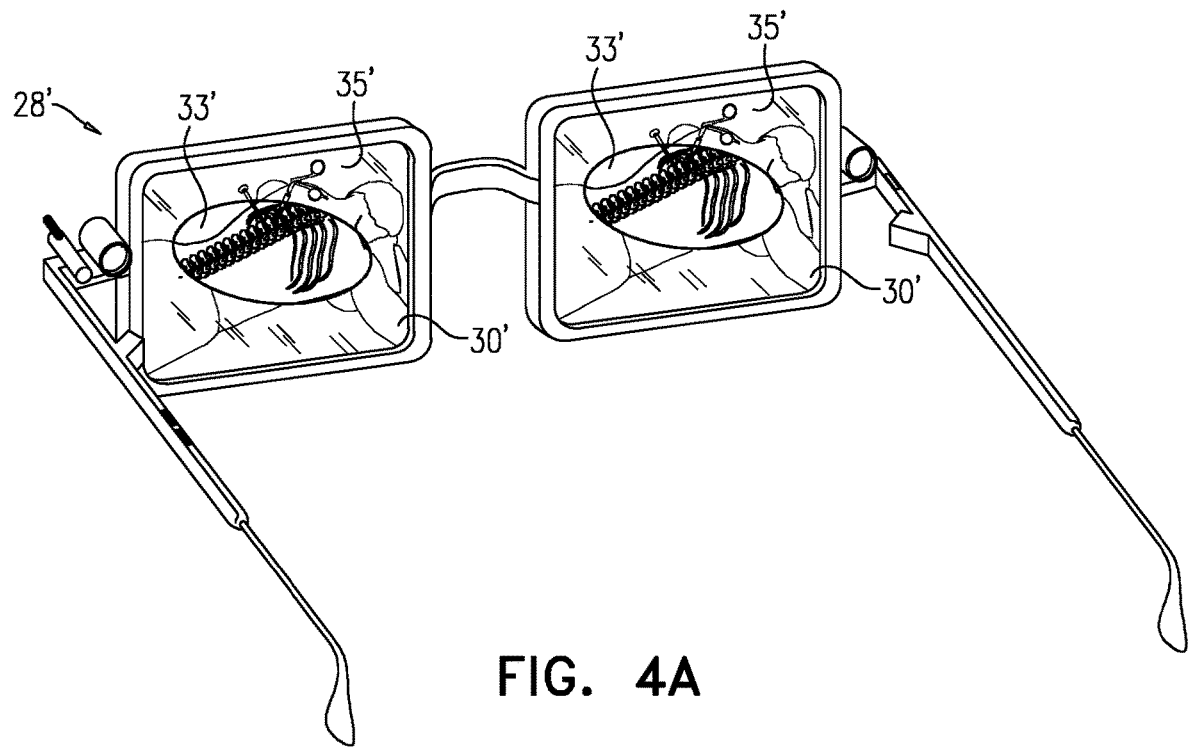
FIGS. 4A and 4B are schematic illustrations of examples of displays of head-mounted devices as worn by respective healthcare professionals, when the line of sight between a tracking device of one of the healthcare professionals with respect to a patient marker is at least partially blocked, in accordance with some applications of the present invention.
Figure 4B:
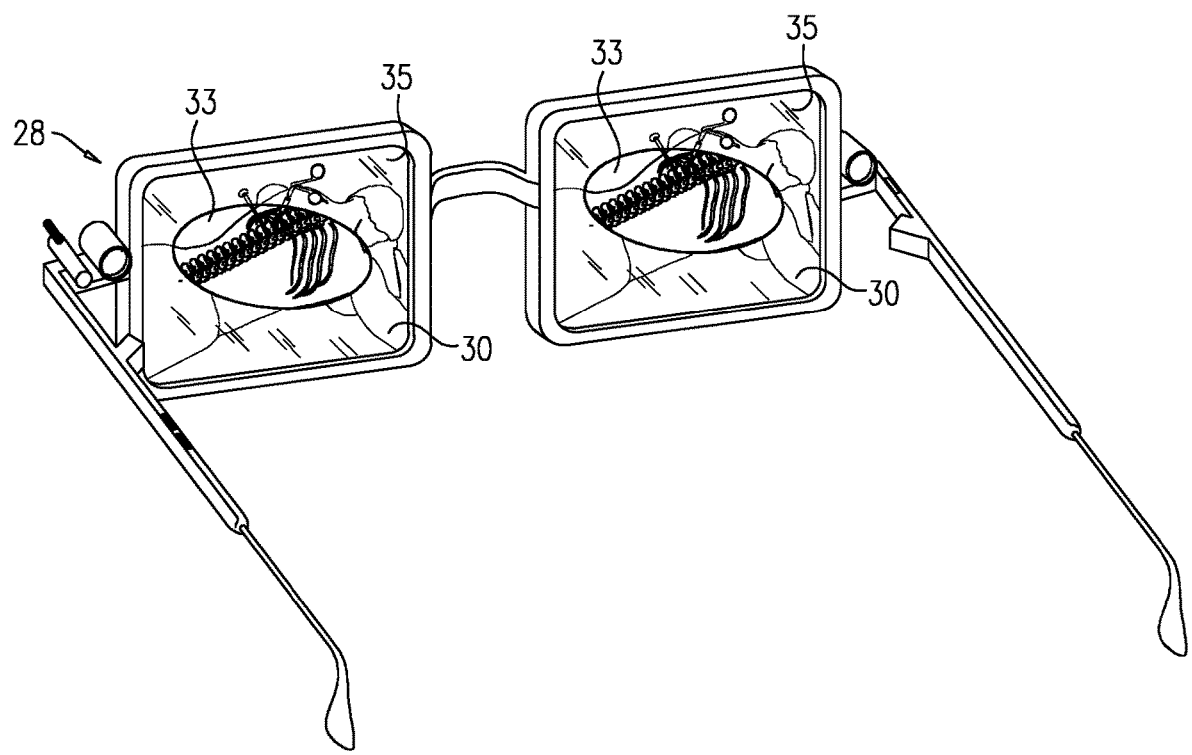

Reference is now made to FIGS. 4A and 4B, which are schematic illustration of examples of displays 30', 30 of head-mounted devices 28', 28 as worn by respective healthcare professionals 26', 26, when the line of sight between tracking device 34 of first healthcare professional 26 with respect to patient marker 38 is at least partially blocked, in accordance with some applications of the present invention. FIG. 4A shows an example of display 30' of second healthcare professional 26', who is shown on the right side of the patient in FIG. 1, and FIG. 4B shows an example of display 30 of first healthcare professional 26, who is shown on the left side of the patient in FIG. 1.

For some such applications, the computer processor generates a virtual image upon head-mounted display 30 of first healthcare professional 26 that shows the virtual view of the second healthcare professional 26' (i.e., the second healthcare professional's view of the virtual anatomy and the virtual tool), as determined based upon the data received from second tracking device 34'. For example, the overall view of the second healthcare professional (including both his/her view of the virtual anatomy and the virtual tool, as well as his/her view of the actual patient anatomy) may be displayed upon head-mounted display 30 of the first healthcare professional. Such an example is shown in FIGS. 4A and 4B, which show the head-mounted displays 30 of first healthcare professional 26 showing the same overall view as that of the second healthcare professional 26'.

Figure 5A:
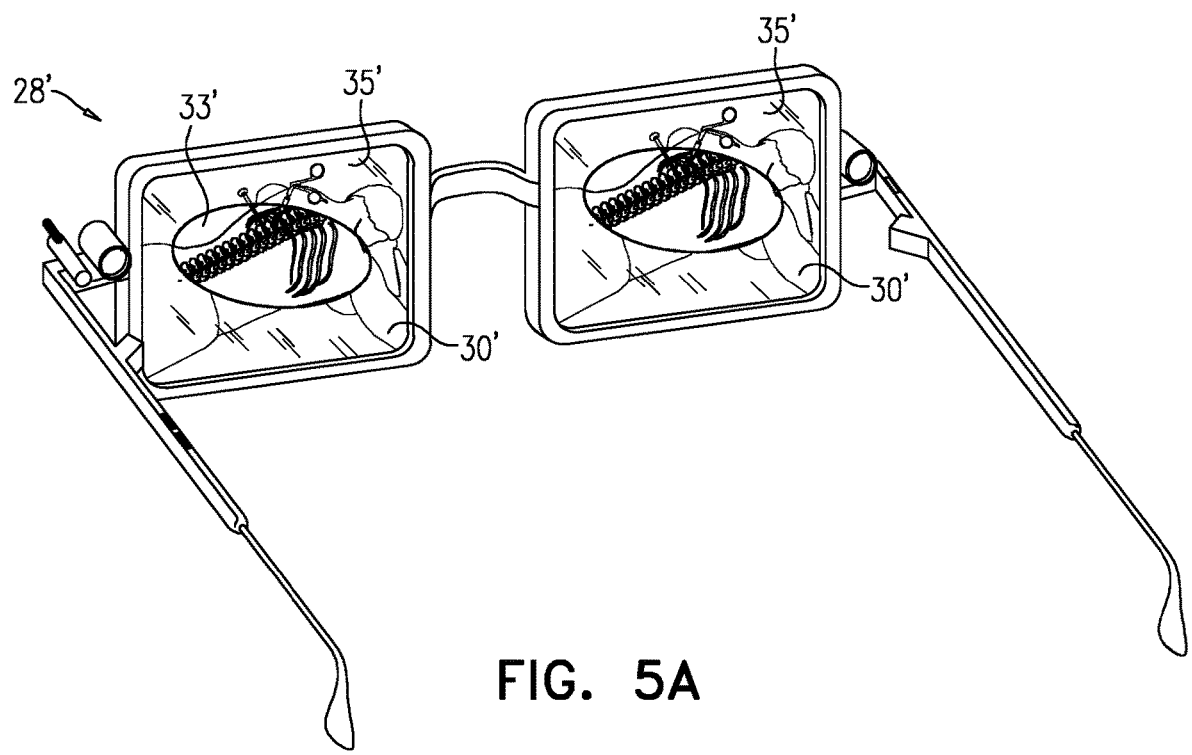
FIGS. 5A and 5B are schematic illustrations of examples of displays of head-mounted devices as worn by respective healthcare professionals, when the line of sight between a tracking device of one of the healthcare professionals with respect to a patient marker is at least partially blocked, in accordance with some applications of the present invention.
Figure 5B:
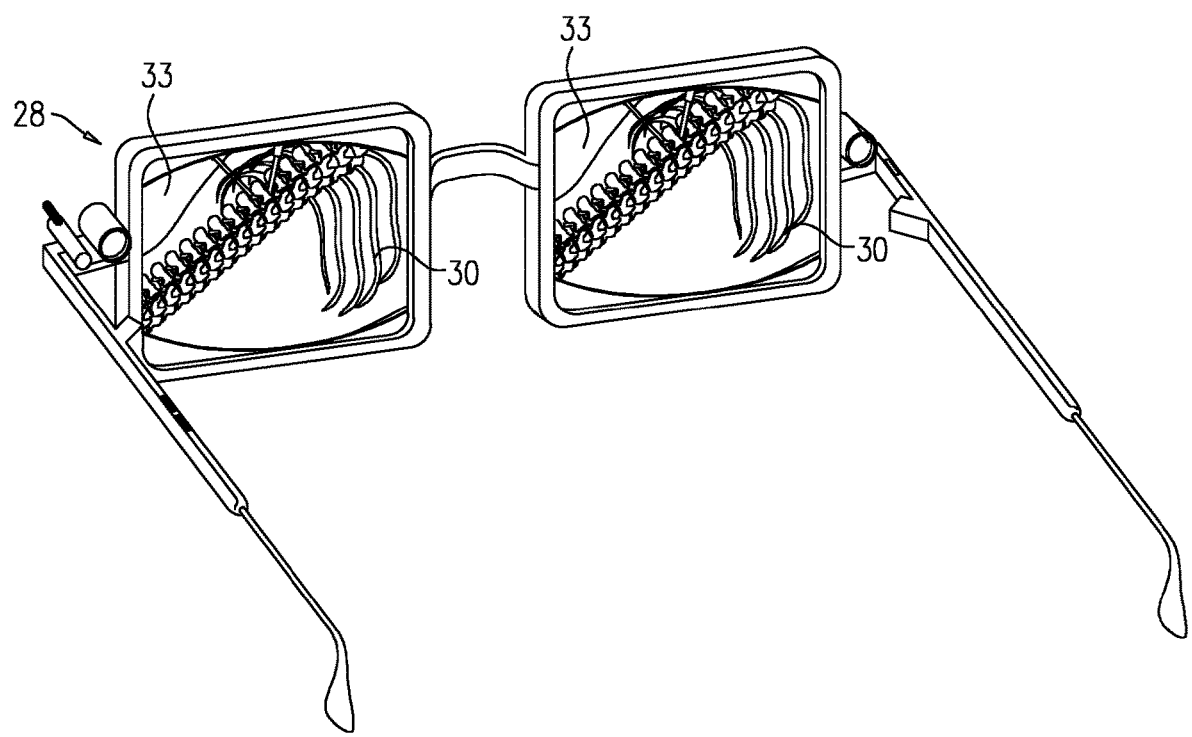

Reference is now made to FIGS. 5A and 5B, which are schematic illustration of examples of displays 30', 30 of head-mounted devices 28', 28 as worn by respective healthcare professionals 26', 26, when the line of sight between tracking device 34 of first healthcare professional 26 with respect to patient marker 38 is at least partially blocked, in accordance with some applications of the present invention. FIG. 5A shows an example of display 30' of second healthcare professional 26', who is shown on the right side of the patient in FIG. 1, and FIG. 5B shows an example of display 30 of first healthcare professional 26, who is shown on the left side of the patient in FIG. 1. For some applications, when the line of sight between tracking device 34 of first healthcare professional 26 with respect to patient marker 38 is at least partially blocked, the virtual image (of the tool and the anatomy) from the line of sight of the second healthcare professional is displayed, such that it fills substantially the whole head-mounted display 30 of the first healthcare professional, and the first healthcare professional is not be shown any of the actual patient anatomy via a transparent portion of the display. An example of such an embodiment is shown in FIGS. 5A and 5B, which show the virtual image from head-mounted displays 30' (shown in FIG. 5A) displayed within portion 33 of the head-mounted displays 30 of the first healthcare professional, and portion 33 filling substantially the whole of head-mounted displays 30 of the first healthcare professional (shown in FIG. 5B).

Figure 6A:
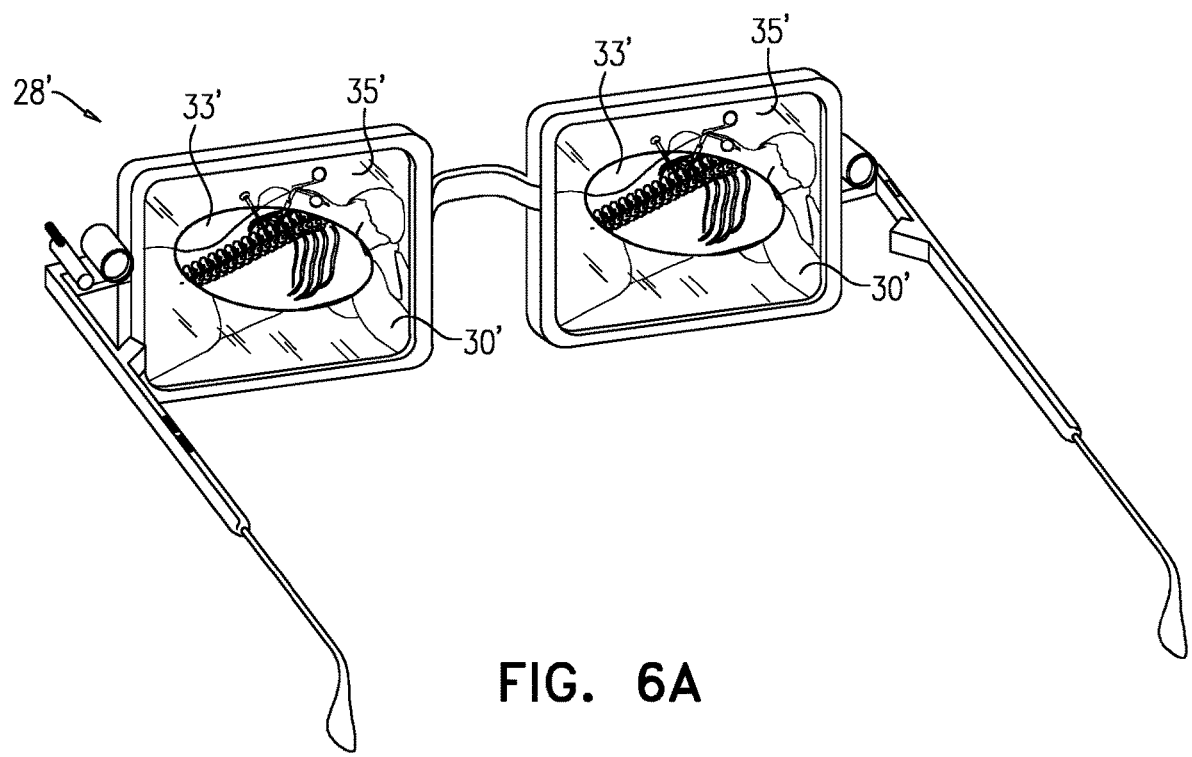
FIGS. 6A and 6B are schematic illustration of examples of displays of head-mounted devices as worn by respective healthcare professionals, when the line of sight between a tracking device of one of the healthcare professionals with respect to a patient marker is at least partially blocked, in accordance with some applications of the present invention.
Figure 6B:
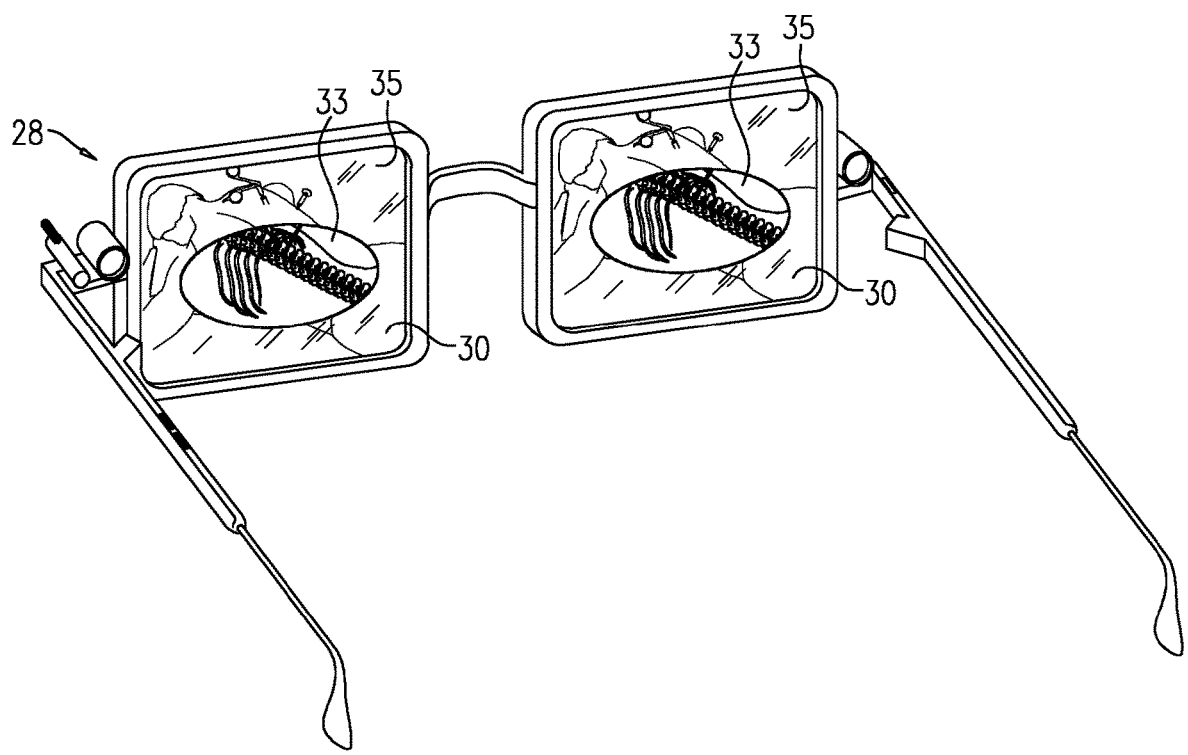

Reference is now made to FIGS. 6A and 6B, which are schematic illustration of examples of displays 30', 30 of head-mounted devices 28', 28 as worn by respective healthcare professionals 26', 26, when the line of sight between tracking device 34 of first healthcare professional 26 with respect to patient marker 38 is at least partially blocked, in accordance with some applications of the present invention. FIG. 6A shows an example of display 30' of second healthcare professional 26', who is shown on the right side of the patient in FIG. 1, and FIG. 6B shows an example of display 30 of first healthcare professional 26, who is shown on the left side of the patient in FIG. 1. For some applications, in response to detecting that tracking device 34 has lost its line of sight of the patient marker, such that the location and/or orientation of the head-mounted device relative to the patient cannot be determined to a given level of accuracy using tracking device 34, the computer processor generates an image of the virtual tool within the virtual anatomy of the subject, but without regard to aligning the computer-generated image with the actual patient anatomy. For some such applications, the virtual image that is generated in portion 33 of display 30 of the first healthcare professional continues to be shown from the first healthcare professional's previous known line of sight, but the position of the tool with respect to the anatomy is updated based upon data received from tracking device 34'. Second portion 35 of the display of the first healthcare professional is kept transparent such that the first healthcare professional sees the patient's anatomy from his/her own current line of sight. An example of such an embodiment is shown in FIGS. 6A and 6B. As shown in FIG. 6B, since changes in the location of head-mounted device 28 with respect to the patient marker are not tracked and accounted for, this may result in a slight misalignment of the virtual image (shown in portion 33) with respect to the patient's body (shown in portion 35). In this regard, it is noted that, in general, the first healthcare professional uses the virtual image of the tool overlaid upon the virtual image of the patient's anatomy, for navigation of the tool. As such, the healthcare professional is typically able to continue to navigate the tool, even though the virtual image of the tool and the patient's anatomy is not aligned with his/her view of the patient's anatomy.

For some applications, generally similar techniques to those described in the above paragraph are performed, but with the additional tracking data that is used for generating an image on head-mounted display 30 being received from tracking device 60, as an alternative to, or in addition to, being received from tracking device 34' of second head-mounted device 28'.

For some applications, in response to detecting that tracking device 34 has lost its line of sight of the tool marker, such that the location and/or orientation of the tool with respect to the patient cannot be determined to a given level of accuracy, the computer processor determines the location of the tool relative to the patient, using data received from tracking device 34' and/or tracking device 60. Typically, a virtual image, which includes the virtual patient anatomy and the virtual tool shown at its current location, is displayed on head-mounted display 30' of head-mounted device 28, with the current location of the tool with respect to the patient having been determined based upon the data received from tracking device 34' and/or tracking device 60.

For some applications, the computer processor is configured to incorporate tracking data that is received from an additional tracking device (i.e., a tracking device in addition to tracking device 34) in order to generate an image upon head-mounted display 30 of first head-mounted device 28, even when the patient marker and the tool marker are within the line of sight of tracking device 34. For some applications, the computer processor determines the location of the tool with respect to the patient, using a combination of data received from tracking device 34' and data received from tracking device 34, and/or using a combination of data received from tracking device 60 and data received from tracking device 34. For example, the computer processor may determine an average (e.g., a mean) current location of the tool with respect to the patient, using the aforementioned combinations of received data, and the computer processor may the generate an image of a virtual tool on virtual anatomy upon head-mounted display 30, in which the tool is positioned at the determined current position.

For some applications, even if a portion of the tracking elements on the patient marker become obscured such that they are not within the line of sight of tracking device 34, the computer processor continue to track the location of the head-mounted device with respect to the patient by tracking the marker using a tracking algorithm (e.g., using a Kalman filter). Typically, in such cases, at least while the patient marker is partially obscured, the computer processor does not continue to actively identify the marker. Rather, the computer processor continues to track the already-identified marker using the aforementioned tracking algorithm. For some applications, if the patient marker becomes obscured (e.g., partially obscured or fully obscured) such that at least a portion of the patient marker is not within the line of sight of tracking device 34, the computer processor continues to determine the location of the patient relative to the head-mounted device, using inertial measurement unit 44, in combination with the last location of the patient marker as determined using data from tracking device 34.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 32 and/or 45. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 32 and/or 45) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the algorithms described herein, can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 32 and/or 45) or other programmable data processing apparatus, create means for implementing the functions/acts specified in the algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the algorithms described in the present application.

Computer processor 32 and/or computer processor 45 is typically a hardware device programmed with computer program instructions to produce a special purpose computer. For example, when programmed to perform the algorithms described with reference to the figures, computer processor 32 and/or 45 typically acts as a special purpose image-generating computer processor. Typically, the operations described herein that are performed by computer processor 32 and/or 45 transform the physical state of a memory, which is a real physical article, to have a different magnetic polarity, electrical charge, or the like depending on the technology of the memory that is used. For some applications, operations that are described as being performed by a computer processor are performed by a plurality of computer processors in combination with each other.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with a tool configured to be placed within a portion of a body of a patient, the method comprising:
tracking the tool and a patient marker that is placed upon the patient's body from a first line of sight, using a first tracking device that is disposed upon a first head-mounted device that is worn by a first person, the first head-mounted device including a first head-mounted display;
tracking the tool and the patient marker, from a second line of sight, using a second tracking device; and
using at least one computer processor for:
generating an augmented reality image upon the first head-mounted display based upon data received from the first tracking device and without using data from the second tracking device, the augmented reality image including (a) a virtual image of the tool and anatomy of the patient, overlaid upon (b) the patient's body;
detecting that the first tracking device no longer has both the patient marker and the tool in the first line of sight;
in response to detecting that the first tracking device no longer has both the patient marker and the tool within the first line of sight, generating the virtual image of the tool and anatomy of the patient upon the first head-mounted display from the first line of sight of the first tracking device worn by the first person, by incorporating data received from the second tracking device with respect to a position of the tool in the body into the virtual image; and
in response to detecting a portion of the tool being within the first line of sight, and a portion of the patient marker not being within the first line of sight:
determining a position of the tool with respect to the anatomy of the patient using data received from the second tracking device; and
generating the virtual image of the tool and anatomy of the patient upon the first head-mounted display, based upon the determined position of the tool with respect to the anatomy of the patient.

2. The method according to claim 1, wherein tracking the tool comprises tracking a tool marker.

3. The method according to claim 1, wherein tracking the tool and the patient marker, from the second line of sight, using the second tracking device, comprises tracking the tool and the patient marker from the second line of sight, using the second tracking device disposed in a stationary position.

4. The method according to claim 1, wherein generating the virtual image of the tool and anatomy of the patient upon the first head-mounted display further comprises overlaying the virtual image upon the patient's body, based upon a position of the patient's body with respect to the first head-mounted device as determined based upon data received from the first tracking device at a time when the portion of the patient marker was within the first line of sight.

5. The method according to claim 4, wherein overlaying the virtual image upon the patient's body comprises tracking movements of the first head-mounted device between the time when the portion of the patient marker was within the first line of sight and the portion of the patient marker not being within the first line of sight, using an inertial-measurement unit disposed upon the first head-mounted device.

6. The method according to claim 1, wherein the second tracking device is disposed upon a second head-mounted device that is worn by a second person.

7. The method according to claim 6, further comprising generating a further augmented-reality image upon a second head-mounted display of the second head-mounted device.

8. The method according to claim 1, wherein the at least one computer processor is configured to generate the virtual image of the tool and anatomy of the patient upon the first head-mounted display by overlaying the virtual image of the tool and the anatomy of the patient upon the patient's body based upon a position of the first head-mounted device with respect to the tool as determined based upon data received from the first tracking device.

9. The method according to claim 1, wherein the virtual image of the tool and anatomy of the patient comprises a virtual image of the tool overlaid on a virtual image of the anatomy of the patient, wherein the virtual image of the tool is aligned with the virtual image of the anatomy of the patient.

10. The method according to claim 1, further comprising generating the virtual image of the tool and anatomy of the patient upon the first head-mounted display when at least the patient marker or the tool is within the first line of sight such that the virtual image of the tool and anatomy of the patient is aligned with actual patient anatomy based upon data received from the first tracking device.

11. A method for use with a tool configured to be placed within a portion of a body of a patient, the method comprising:
tracking the tool and a patient marker that is placed upon the patient's body from a first line of sight, using a first tracking device that is disposed upon a first head-mounted device that is worn by a first person, the first head-mounted device including a first head-mounted display;
tracking the tool and the patient marker, from a second line of sight, using a second tracking device; and
using at least one computer processor for:
generating an augmented reality image upon the first head-mounted display based upon data received from the first tracking device and without using data from the second tracking device, the augmented reality image including (a) a virtual image of the tool and anatomy of the patient, overlaid upon (b) the patient's body;
detecting that the first tracking device no longer has both the patient marker and the tool in the first line of sight;
in response to detecting that the first tracking device no longer has both the patient marker and the tool within the first line of sight, generating the virtual image of the tool and anatomy of the patient upon the first head-mounted display from the first line of sight of the first tracking device worn by the first person, by incorporating data received from the second tracking device with respect to a position of the tool in the body into the virtual image; and
in response to detecting a portion of the patient marker being within the first line of sight, and a portion of the tool not being within the first line of sight:
determining a position of the tool with respect to the anatomy of the patient using data received from the second tracking device;
generating the virtual image of the tool and anatomy of the patient upon the first head-mounted display, based upon the determined position of the tool with respect to the anatomy of the patient;
determining a position of the patient's body with respect to the first head-mounted device based upon data received from the first tracking device; and overlaying the virtual image upon the patient's body, based upon the determined position of the patient's body with respect to the first head-mounted device.

12. The method according to claim 11, wherein the virtual image of the tool and anatomy of the patient comprises a virtual image of the tool overlaid on a virtual image of the anatomy of the patient, wherein the virtual image of the tool is aligned with the virtual image of the anatomy of the patient.

13. The method according to claim 11, further comprising generating the virtual image of the tool and anatomy of the patient upon the first head-mounted display when at least the patient marker or the tool is within the first line of sight such that the virtual image of the tool and anatomy of the patient is aligned with actual patient anatomy based upon data received from the first tracking device.

14. Apparatus for use with a tool configured to be placed within a portion of a body of a patient, the apparatus comprising:
  a first head-mounted device comprising a first head-mounted display, and a first tracking device that is configured to track the tool and a patient marker from a first line of sight, wherein the patient marker is configured to be placed upon the patient's body;
  a second tracking device that is configured to track the tool and the patient marker from a second line of sight; and
  at least one computer processor configured:
  to generate an augmented reality image upon the first head-mounted display, based upon data received from the first tracking device and without using data from the second tracking device, the augmented reality image including (a) a virtual image of the tool and anatomy of the patient, overlaid upon (b) the patient's body;
  after generating the augmented reality image, to detect that the first tracking device no longer has both the patient marker and the tool in the first line of sight;
  in response to detecting that the first tracking device no longer has both the patient marker and the tool within the first line of sight, to generate the virtual image of the tool and anatomy of the patient upon the first head-mounted display from the first line of sight of the first tracking device worn by the first person, by incorporating data received from the second tracking device with respect to a position of the tool in the body into the virtual image; and
  in response to detecting a portion of the tool being within the first line of sight, and a portion of the patient marker not being within the first line of sight:
  to determine a position of the tool with respect to the anatomy of the patient using data received from the second tracking device; and
  to generate the virtual image of the tool and anatomy of the patient upon the first head-mounted display, based upon the determined position of the tool with respect to the anatomy of the patient.

15. The apparatus according to claim 14, wherein the tool includes a tool marker, and wherein the first and second tracking devices are configured to track the tool by tracking the tool marker.

16. The apparatus according to claim 14, wherein the second tracking device comprises a tracking device that is disposed in a stationary position.

17. The apparatus according to claim 14, wherein the at least one computer processor is configured to generate the virtual image of the tool and anatomy of the patient upon the first head-mounted display by overlaying the virtual image upon the patient's body, based upon the position of the patient's body with respect to the first head-mounted device as determined based upon the data received from the first tracking device at a time when the portion of the patient marker was within the first line of sight.

18. The apparatus according to claim 17, further comprising an inertial-measurement unit disposed upon the first head-mounted device, wherein the at least one computer processor is configured to overlay the virtual image upon the patient's body by tracking movements of the head-mounted device between the time when the portion of the patient marker was within the first line of sight and the portion of the patient marker not being within the first line of sight, using data from the inertial-measurement unit.

19. The apparatus according to claim 14, wherein the first head-mounted device is configured to be worn by a first person, the apparatus further comprising a second head-mounted device that is configured to be worn by a second person, and wherein the second tracking device is disposed upon the second head-mounted device.

20. The apparatus according to claim 14, further comprising the patient marker.

21. The apparatus according to claim 14, wherein the at least one computer processor is configured to generate the virtual image of the tool and anatomy of the patient upon the first head-mounted display by overlaying the virtual image of the tool and the anatomy of the patient upon the patient's body based upon a position of the first head-mounted device with respect to the tool as determined based upon data received from the first tracking device.

22. The apparatus according to claim 14, wherein the virtual image of the tool and anatomy of the patient comprises a virtual image of the tool overlaid on a virtual image of the anatomy of the patient, wherein the virtual image of the tool is aligned with the virtual image of the anatomy of the patient.

23. The apparatus according to claim 14, wherein the at least one computer processor is further configured to generate the virtual image of the tool and anatomy of the patient upon the first head-mounted display when at least the patient marker or the tool is within the first line of sight such that the virtual image of the tool and anatomy of the patient is aligned with actual patient anatomy based upon data received from the first tracking device.

24. Apparatus for use with a tool configured to be placed within a portion of a body of a patient, the apparatus comprising:
  a first head-mounted device comprising a first head-mounted display, and a first tracking device that is configured to track the tool and a patient marker from a first line of sight, wherein the patient marker is configured to be placed upon the patient's body;
  a second tracking device that is configured to track the tool and the patient marker from a second line of sight; and
  at least one computer processor configured:
  to generate an augmented reality image upon the first head-mounted display, based upon data received from the first tracking device and without using data from the second tracking device, the augmented reality image including (a) a virtual image of the tool and anatomy of the patient, overlaid upon (b) the patient's body;
  after generating the augmented reality image, to detect that the first tracking device no longer has both the patient marker and the tool in the first line of sight;
  in response to detecting that the first tracking device no longer has both the patient marker and the tool within the first line of sight, to generate the virtual image of the tool and anatomy of the patient upon the first head-mounted display from the first line of sight of the first tracking device worn by the first person, by incorporating data received from the second tracking device with respect to a position of the tool in the body into the virtual image; and in response to detecting a portion of the patient marker being within the first line of sight, and a portion of the tool not being within the first line of sight:

to determine a position of the tool with respect to the anatomy of the patient using data received from the second tracking device;

to generate the virtual image of the tool and anatomy of the patient upon the first head-mounted display, based upon the determined position of the tool with respect to the anatomy of the patient;

to determine a position of the patient's body with respect to the first head-mounted device based upon data received from the first tracking device; and to overlay the virtual image upon the patient's body, based upon the determined position of the patient's body with respect to the first head-mounted device.

25. The apparatus according to claim 24, wherein the virtual image of the tool and anatomy of the patient comprises a virtual image of the tool overlaid on a virtual image of the anatomy of the patient, wherein the virtual image of the tool is aligned with the virtual image of the anatomy of the patient.

26. The apparatus according to claim 24, wherein the at least one computer processor is further configured to generate the virtual image of the tool and anatomy of the patient upon the first head-mounted display when at least the patient marker or the tool is within the first line of sight such that the virtual image of the tool and anatomy of the patient is aligned with actual patient anatomy based upon data received from the first tracking device.

* * * * *